US009310384B2

(12) United States Patent
Sandau et al.

(10) Patent No.: US 9,310,384 B2
(45) Date of Patent: Apr. 12, 2016

(54) FELINE BITTER TASTE RECEPTORS AND METHODS

(71) Applicant: Applied Food Biotechnology, Inc., St. Charles, MO (US)

(72) Inventors: Michelle M. Sandau, Saint Charles, MO (US); Nancy E. Rawson, Chesterfield, MO (US)

(73) Assignee: APPLIED FOOD BIOTECHNOLOGY, INC., St. Charles, MO (US)

( * ) Notice: Subject to any disclaimer, the term of this patent is extended or adjusted under 35 U.S.C. 154(b) by 0 days.

(21) Appl. No.: 14/850,013

(22) Filed: Sep. 10, 2015

(65) Prior Publication Data

US 2016/0003852 A1    Jan. 7, 2016

Related U.S. Application Data

(62) Division of application No. 14/198,795, filed on Mar. 6, 2014, now Pat. No. 9,169,311.

(60) Provisional application No. 61/788,528, filed on Mar. 15, 2013.

(51) Int. Cl.
| C07K 14/705 | (2006.01) |
| C07K 16/28 | (2006.01) |
| G01N 33/50 | (2006.01) |
| G01N 33/74 | (2006.01) |
| C12N 9/96 | (2006.01) |

(52) U.S. Cl.
CPC .............. *G01N 33/74* (2013.01); *C07K 14/705* (2013.01); *C12N 9/96* (2013.01); *C07K 2319/61* (2013.01); *G01N 2333/726* (2013.01); *G01N 2500/04* (2013.01)

(58) Field of Classification Search
None
See application file for complete search history.

(56) References Cited

U.S. PATENT DOCUMENTS

| 7,022,488 | B2 | 4/2006 | Servant et al. |
| 7,413,867 | B2 | 8/2008 | Bufe et al. |
| 7,527,944 | B2 | 5/2009 | Li et al. |
| 7,541,158 | B2 | 6/2009 | Li et al. |
| 8,071,719 | B2 | 12/2011 | Zoller et al. |
| 8,158,442 | B2 | 4/2012 | Bufe et al. |
| 8,187,822 | B2 | 5/2012 | Brune et al. |
| 8,273,542 | B2 | 9/2012 | Li et al. |
| 8,309,314 | B2 | 11/2012 | Behrens et al. |
| 8,309,701 | B2 | 11/2012 | Drayna et al. |
| 8,334,367 | B2 | 12/2012 | Adler |
| 2004/0214239 | A1 | 10/2004 | Servant et al. |
| 2011/0281753 | A1 | 11/2011 | Moyer et al. |
| 2011/0311991 | A1 | 12/2011 | Slack et al. |
| 2012/0015841 | A1 | 1/2012 | Shekdar et al. |
| 2013/0030059 | A1 | 1/2013 | Li et al. |

FOREIGN PATENT DOCUMENTS

| WO | 0118050 A2 | 3/2001 |
| WO | 2006053771 A2 | 5/2006 |
| WO | 2011012298 A1 | 2/2011 |
| WO | 2011050955 A1 | 5/2011 |
| WO | 2012013480 A1 | 2/2012 |
| WO | 2014149829 A1 | 9/2014 |

OTHER PUBLICATIONS

Bachmanov AA et al. "Taste Receptor Genes"; NIH Public Access Author Manuscript; available in PMC Aug. 5, 2009 (Published in final edited form as: Annu Rev Nutr.; 2007; 27:389-414); 26 pgs.
Behrens M. et al. "Bitter taste receptor research comes of age: From characterization to modulation of TAS2Rs". Semin Cell Dev Biol (2012), http://dx.doi.org/10.1016/j.semcdb.2012.08.006; Epub Aug. 27, 2012 (7 pages).
Conte et al.; "Evolutionary relationships of the Tas2r receptor gene families in mouse and human"; Physiol Genomics, 14; 2003; pp. 73-82.
Conte; "Functional expression of mammalian bitter taste receptors in Caenorhabditis elegans"; Biochimie 88; 2006; 801-806.
Dong D. et al. "Dynamic Evolution of Bitter Taste Receptor Genes in Vertebrates" BMC Evolutionary Biology 2009,9:12 doi:10.1186/1471-2148-9-12 (9 pages).
Go Y. et al. "Lineage-Specific Loss of Function of Bitter Taste Receptor Genes in Humans and Nonhuman Primates"; Genetics; May 2005; 170: 313-326.
Go; :Lineage-specific expansions and contractions of the bitter taste receptor gene repertoire in vertebrates; Mol. Biol. Evol., 23; 2006; 964-972.
Imai H. et al. "Functional Diversity of Bitter Taste Receptor TAS2R16 in Primates" Biol Lett. Aug. 23, 2012;8(4):652-6. doi: 10.1098/rsbl.2011.1251. Epub Mar. 7, 2012.
International Search Report; International Application No. PCT/US2014/021110; Filing Date: Mar. 6, 2014; Mailing Date: Jul. 11, 2014; 7 pgs.
Jiang et al.; "Major taste loss in carnivorous mammals"; PNAS, vol. 109 No. 13;2012; pp. 4956-4961.
Li H. et al. "Selection on the Human Bitter Taste Gene, TAS2R16, in Eurasian Populations" Human Biology vol. 83, Issue 3, Article 3, 2011 (17 pages); Available at: http://digitalcommons.wayne.edu/humbiol/vol83/iss3/3.
Mueller et al.; "The receptors and coding logic for bitter taste"; Nature, 434; 2005; pp. 225-229.

(Continued)

Primary Examiner — John Ulm
(74) Attorney, Agent, or Firm — Cantor Colburn LLP

(57) ABSTRACT

A family of novel feline bitter taste receptors, referred to as feline TAS2R (fTAS2R), are disclosed herein. Isolated polynucleotides encoding the novel feline bitter taste receptors and chimeric polypeptides are also disclosed, as are expression vectors and host cells for expression of the novel feline bitter taste receptors. Methods of identifying compounds that bind to the novel feline bitter taste receptors and modulate their activity are disclosed.

20 Claims, 2 Drawing Sheets

(56) References Cited

OTHER PUBLICATIONS

Mullikin JC et al.; "Light whole genome sequence for SNP discovery across domestic cat breeds" BMC Genomics;2010; 11: 406; 8 pages.
NCBI Reference Sequence: XP_003988467.1; Nov. 6, 2012; Predicted, Low quality protein: taste receptor type 2 member 20-like [Felis catus]; 1 pg.
Pontius Ju et al.; Initial sequence and comparative analysis of the cat genome: Genome Res.; 2007; 17:1675-1689.
Third-Party Pre-issuance submission under 37 CFR 1.290, Concise Description of Relevance, submitted in U.S. Appl. No. 14/198,795 on Mar. 17, 2015 (8 pages).
Ueda et al.; "Functional Interaction between T2R Taste Receptors and G-Protein α Subunits Expressed in Taste Receptor Cells"; The Journal of Neuroscience, 23(19); 2003; 7376-7380.
Written Opinion dated Jul. 11, 2014; International Application No. PCT/US2014/021110; Filing Date: Mar. 6, 2014; 8 pgs.
XP002725495; NCBI Reference Sequence: XP_003981606.1; Nov. 6, 2012; Predicted: taste receptor type 2 member 1-like [Felis catus]; 1 pg.
XP002725979; NCBI Reference Sequence: XP_003982855.1; Nov. 6, 2012;Predicted: taste receptor type 2 member 7-like [Felis catus]; 1 pg.
XP002725980; NCBI Reference Sequence: XP_003983201.1; Nov. 6, 2012; Predicted: taset receptor type 2 member 3-like [Felis catus]; 1 pg.
XP002725981; NCBI Reference Sequence: XP_003983202.1; Nov. 6, 2012; Predicted: taste receptor type 2 member 4-like [Felis catus]; 1 pg.
XP002725982; NCBI Reference Sequence: XP_003988464.1; Nov. 6, 2012; Predicted: taste receptor type 2 member 7-like [Felis catus]; 1 pg.
XP002725983; NCBI Reference Sequence: XP_003988514.1; Nov. 6, 2012; Predicted: taste receptor type 2 member 9-like [Felis catus]; 1 pg.
XP002725984; NCBI Reference Sequence: XP_003988465.1; Nov. 6, 2012; Predicted: taste receptor type 2 member 10-like [Felis catus]; 1 pg.
XP002725985; NCBI Reference Sequence: XP_003988515.1; Nov. 6, 2012; Predicted: taste receptor type 2 member 7-like [Felis catus]; 1 pg.
XP002725986; NCBI Reference Sequence: XP_003983168.1; Nov. 6, 2012; Predicted: taste receptor type 2 member 38-like [Felis catus]; 1 pg.
XP002725987; NCBI Reference Sequence: XP_003988470.1; Nov. 6, 2012; Predicted: taste receptor type 2 member 42-like [Felis catus]; 1 pg.
XP002725988; NCBI Reference Sequence: XP_003988466.1; Nov. 6, 2012; Predicted: taste receptor type 2 member 46-like [Felis catus]; 1 pg.
XP002725989; NCBI Reference Sequence: XP_003988469.1; Nov. 6, 2012; Predicted: taste receptor type 2 member 42-like [Felis catus]; 1 pg.
XP002725990: retrived from EBI Database accession No. ENSFCAP00000024300; Jan. 2013; 1 pg.
Xu H et al. "Molecular Cloning and Evolutionary Analysis of Hog Badger Bitter Taste Receptor T2R2 Gene"; Hereditas (Beijing); 2009, 31(11): 1113-1120. DOI: 10.3724/SP .J.1005.2009.01113.

FIG. 1

```
                          TM 3  110         120         130         140   TM 4 150
human Tas2R16                   WFFFNLTFWNSLLIVFYC KVSSFTHHI FLWLRWRI LRLFPWLLGSL  134
human Tas2R4                    FMFLDSSSVWFVTLLNI LYCVKI TNFQHSVFLLLKRNI SPKI PRLLLACV  137
feline Tas2R4                   WMFLESTSLWLVTLLNALYCVKI TDFQHSVFLLLKRKLSPKI PRLLLACV  138
human Tas2R9                    WTFANNSSLWFTSCLSI FYLLKI ANI SHPFFFWLKLKI NKVMLAI LLGSF  138
feline Tas2R9                   WTLSNHSSVWFTACLSI FYLLKI ANI SHPVFLWLKLNVTRVVLGLFLASF  138
human Tas2R10                   WVI GNQSSMWFATSLSI FYFLKI ANFSNYI FLWLKSRTNMV- LPFMI VFL  136
feline Tas2R10                  WI I I NQSNI WFATSLSTFYFLKI ANFSHHMFLWLKGRI NW- LPLLMGSL  137
feline Tas2R12                  WTGSNYFCI TCTTCLSVFYFFKI ANFSNPLFLW KWRI HKVLLTI VLAAV  138
human Tas2R38                   WMI ANQANLWLAACLSLLYCSKLI RFSHTFLI CLASWVSRKI SQMLLGI I  148
feline Tas2R38                  WMI TNQVGLWLTTCLSLLYCSKI ARFSHTLLHCVASWVSRKVPQMLLGAM  148

TM 4  160         170         180         190         200
human Tas2R16                   MI TCVTI I PSAI GNYI QI QLLTMEHLPRNSTVTDKLENFHQYQFQAHT- -  182
human Tas2R4                    LI SAFTTCLYI TLSQASP- - - FPELVTTRNNTSFNI SEGI LSLVVSLV- -  182
feline Tas2R4                   LI SAFSTLLYVVLTQTSP- - - FPELLTGSNGTVCDI NKSI LSLVTSLV- -  183
human Tas2R9                    LI SLI I SVPKNDDMWYHL- - - FKVSHEENI TWKFKVSKI PG- - TFKQLTL  183
feline Tas2R9                   LTSI I I SVFLKEGSWGHV- - - - EVNHEENI TWEFRVSKAPS- - AFKLI I L  182
human Tas2R10                   LI SSLLNFAYI AKI LND- - - - YKT- KNDTV- WDLNMYKSEY- - FI KQI LL  178
feline Tas2R10                  FI SWLFTFPQI VKI LSD- - - - SKVGNGNAT- WQLNMPKSEF- - LTKQI LV  180
feline Tas2R12                  F- SFCLSLPFKDTVFTSL- - - I KNKVNAERNWTVSFTTRTYELFLSHMLL  184
human Tas2R38                   LCSCI CTVLCVWCFFSRPHFTVTTVLFMNNNTRLNWQI KDLNLFYSFLFC  198
feline Tas2R38                  LFSCI CTAI CLGDFFSRSGFTFTTMLFVNN- TEFNLQI AKLSFYHSFI FC  197

TM 5  210         220         230         240         250
human Tas2R16                   - VALVI PFI LFLAST FLMASI - - - TKQI QHHSTGHCNPSMKARFTALRS  228
human Tas2R4                    - LSSSLQFI I NVTSASLLI HSLRRHI QKMQKNATGFWNPQTEAHVGAMKL  231
feline Tas2R4                   - LSSFLQFI MNVTSASLLI HSLRRHI QKMQKNATDFWNPQTEAHMGAMKL  232
human Tas2R9                    NLGVMVPFI LCLI SFFLLLFSLVRHTKQI RLHATGFRDPSTEAHMRAI KA  233
feline Tas2R9                   NLGALVPFALCLI SFVLLLFSLFRHAKQMQLYATGSRDCSTEAHMRAI KA  232
human Tas2R10                   NLGVI FFFTLSLI TCI FLI I SLWRHNRQMQSNVTGLRDSNTEAHVKAMKV  228
feline Tas2R10                  NI GVLLLFTLFLI TCFLLI I SLWRHSRRMQLNVTGFQDPSTEAHMKAMKV  230
feline Tas2R12                  NI MFI I PFAVSLASFVLLI CSLWSHTRQMKGRGG- - - DPTTKVHVRAMKA  231
human Tas2R38                   YLWSVPPFLLFVSSGMLTVSLGRHMRTMKVYTRNSRDPSLEAHI KALKS  248
feline Tas2R38                  TLASI PSLLFFLI SSGVLI VSLGRHMRTMRAKTKDSHDPSLEAHI KALRS  247

TM 6  260         270         280    TM 7  290         300
human Tas2R16                   AVLI I VFTSYFLTLI LI I I GTLF- DKRCW WVEAI YAFLLMI STSLH  277
human Tas2R4                    MVYFLI LYI PYSVATLVQYLPFYAGMDMGTKSI CLI FATLYSPGHSVLI I  281
feline Tas2R4                   MI YFLI LYI PYSLATLLQYLPS- VRMDLGATSI CMI I STFYPPGHSVLI I  281
human Tas2R9                    VI I FLLLLI VYYPVFLVMTSSALI PQGKLVLMI GDI VTVI FPSSHSFI LI  283
feline Tas2R9                   VTI FLLFFI MYYAVFLVVTSSFLI PQGRVVLMFGGI VTVI FPSSHSFI LI  282
human Tas2R10                   LI SFI I LFI LYFI GMAI EI SCFTVRENKLLLMFGMTTTAI YPWGHSFI LI  278
feline Tas2R10                  LI SFI I LFI LHFI GLAI EI ACFTMPEKKLLFI FGMTTTVLYPWGHSFI LI  280
feline Tas2R12                  MI SFLLFFFMYYLSTI MMNLAYVI LDSLVAKI FANTLVFLYPSGHTFLLI  281
human Tas2R38                   LVSFFCFFVI SSCVAFI SVPLLI LWRDKI GVMVCVGI MAACPSGHAAI LI  298
feline Tas2R38                  LVSFLCLYVVSFCAALVSVPLLMLWHNKI GVMI CVGI LAACPSI HAAI LI  297
```

FIG. 2

```
                        10           20           30           40           50
                        |            |            |            |            |
feline Tas2R38   MLALTPVITVSYEVKSAFLFLSILEFTVGVLANAFIFLVNFWDVVRKQ L   50
human Tas2R38    MLTLTRIRTVSYEVRSTFLFISVLEFAVGFLTNAFVFLVNFWDVVKRQ L   50

60           70           80           90          100
                        |            |            |            |            |
feline Tas2R38   SNCDLILLSLSLTRLFLHGLLFLDALQLTYFQRMKDPLSLSYQTIIMLWM 100
human Tas2R38    SNSDCVLLCLSISRLFLHGLLFLSAIQLTHFQKLSEPLNHSYQAIIMLWM 100

110          120          130          140          150
                        |            |            |            |            |
feline Tas2R38   ITNQVGLWLTTCLSLLYCSKIARFSHTLLHCVASWVSRKVPQMLLGAMLF 150
human Tas2R38    IANQANLWLAACLSLLYCSKLIRFSHTFLICLASWVSRKISQMLLGIILC 150

160          170          180          190          200
                        |            |            |            |            |
feline Tas2R38   SCICTAICLGDFFSRSGFTFTTMLFVNN-TEFNLQIAKLSFYHSFIFCTL 199
human Tas2R38    SCICTVLCVWCFFSRPHFTVTTVLFMNNNTRLNWQIKDLNLFYSFLFCYL 200

210          220          230          240          250
                        |            |            |            |            |
feline Tas2R38   ASIPSLLFFLISSGVLIVSLGRHMRTMRAKTKDSHDPSLEAHIKALRSLV 249
human Tas2R38    WSVPPFLLFLVSSGMLTVSLGRHMRTMKVYTRNSRDPSLEAHIKALKSLV 250

260          270          280          290          300
                        |            |            |            |            |
feline Tas2R38   SFFCLYVVSFCALVSVPLLMLWHNKIGVMICVGILAACPSIHAALISG   299
human Tas2R38    SFFCFFVISSCAFISVPLLILWRDKIGVMVCVGIMAACPSGHAALISG   300

310          320          330
                        |            |            |
feline Tas2R38   NAKLRRAVETILLWQNSLKIGADHKADARTPGLC            335
human Tas2R38    NAKLRRAVMTILLWAQSSLKVRADHKADSRTL---C           333
```

FELINE BITTER TASTE RECEPTORS AND METHODS

CROSS REFERENCE TO RELATED APPLICATIONS

This application is a division of U.S. patent application Ser. No. 14/198,795, filed Mar. 6, 2014, which claims the benefit of U.S. Provisional Application No. 61/788,528, filed Mar. 15, 2013, the disclosure of each is incorporated herein by reference.

SEQUENCE LISTING

This application includes a sequence listing, incorporated herein by-reference in its entirety, submitted electronically with the application via EFS-WEB as an ASCII text file of 65 kB named 714409002 and created Feb. 18, 2014.

BACKGROUND

The taste system provides sensory information about the chemical composition of the external world. Mammals are believed to have at least five basic taste modalities: sweet, bitter, sour, salty, and umami. Each taste modality is thought to be mediated by a distinct protein receptor or receptors that are expressed in taste receptor cells found on the surface of the tongue. The taste receptors that recognize bitter, sweet, and umami taste stimuli belong to the G-protein-coupled receptor (GPCR) superfamily. Subtle differences in a receptor may alter which ligands bind and what signal is generated once the receptor is stimulated.

Various members of the GPCR superfamily mediate many other physiological functions, such as endocrine function, exocrine function, heart rate, lipolysis, and carbohydrate metabolism. The biochemical analysis and molecular cloning of a number of such receptors has revealed many basic principles regarding the domain structure and function of these receptors.

The ability of mammals to taste the five primary modalities is thought to be largely similar, however due to diet and environmental differences, taste receptors have evolved to be somewhat different across mammalian species. For example, the gene encoding the TAS1R2 protein, a component of the receptor for sweet compounds, has mutated to a nonfunctional pseudogene in felines and several other obligate carnivores, while aquatic mammals such as dolphin have lost most functional taste receptors.

The bitter taste modality is usually described as disagreeable. Many natural and synthetic toxins have been characterized as bitter tastants. As a result, it is hypothesized that bitter taste perception has evolved as a means to discourage the consumption of toxic compounds often found in plants. Estimates for the number of bitter tasting compounds are in the tens of thousands. However, only 550 compounds have been identified thus far as bitter tastants for humans. Compounds that block bitter taste perception have also been identified, for example p-(dipropylsulfamoyl)benzoic acid (probenecid) which acts on a subset of TAS2Rs.

The perception of bitter taste is mediated by TAS2R proteins, a family of monomeric G protein-coupled receptors, embedded in the surface of taste cells.

Research has shown that molecular diversity in the TAS2Rs of humans and other primates leads to functional differences in individuals' bitter taste perception (Imai et al., 2012, Biol Lett. 8(4): 652-656; Li et al., 2011, Human biology 83: 363-377). The exposure to the specific flora of a geographic region is thought to be a major driving force of selection on TAS2Rs.

Humans encode about 26 functional TAS2Rs, allowing for the detection of an enormous number of compounds. A subset of human TAS2Rs (hTAS2Rs) are currently believed to be promiscuous, i.e., activated by multiple ligands belonging to several chemical classes, while other hTAS2Rs bind ligands of only particular chemical classes. Additionally, several hTAS2Rs are orphan receptors, with no compounds identified as yet that stimulate them.

Signal transduction of bitter stimuli is accomplished via the α-subunit of gustducin. This G protein subunit activates a taste phosphodiesterase and decreases cyclic nucleotide levels. Further steps in the transduction pathway are still unknown. The βγ-subunit of gustducin also mediates taste by activating IP3 (inositol triphosphate) and DAG (diglyceride). These second messengers may open gated ion channels or may cause release of internal calcium. Though all TAS2Rs are located in gustducin-containing cells, knockout of gustducin does not completely abolish sensitivity to bitter compounds, suggesting a redundant mechanism for bitter tasting.

hTAS2R38 is the most extensively studied bitter taste receptor. Early in the twentieth century a dichotomy in the perception of phenylthiocarbamide (PTC), a bitter tasting compound, was observed in a sample of people. Most people could taste PTC, but about 25% could not. Researchers noticed the taster/non-taster phenotype had a degree of heritability. Later it was determined that the difference in phenotype between the two groups could be ascribed to a difference in genotype, more specifically single nucleotide polymorphisms (SNPs) at three positions within the hTAS2R38 DNA.

Other species display a TAS2R repertoire much different from that of humans. For example, the mouse has 34 full-length TAS2Rs encoded in its genome, while the chicken has only 3 (Go, et al. Genetics. 2005 May; 170(1):313-26). Although some compounds can be detected by multiple TAS2Rs, it is almost certain that differences in TAS2R repertoire across species result in differences in bitter taste perception.

The feline genome has been sequenced with minimal coverage. (Mullikin et al. BMC Genomics 2010 11: 406; Pontius et al., Genome Research 2007 17: 1675-1689). As a result, major gaps exist in the feline genome sequence and only slightly over 2000 feline genes have been annotated to date. As a comparison, the human genome has about 25,000 genes annotated. The sequences prior to a gap in the genomic assembly are of poor quality, so in addition to information that is missing, a large portion of the data present is of poor quality. Consequently, there is much to be discovered within feline genomics and in determining the molecular basis of feline taste perception. Not a single feline TAS2R (fTAS2R) has been annotated in the feline genome or investigated biochemically to our knowledge. Additionally, with many feline breeds originating in a particular geographic region and therefore being exposed to unique flora, breed specific TAS2R differences may exist.

There is therefore a need in the art for the identification and characterization of the feline TAS2R bitter receptors in order to understand the taste profile of felines and its modulation.

SUMMARY

Disclosed herein is an isolated polynucleotide encoding a TAS2R receptor.

In an embodiment, the isolated polynucleotide comprises the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25; a nucleotide sequence encoding the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; a nucleotide sequence substantially complementary to the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25; or a nucleotide sequence that hybridizes to the complement of the polynucleotide having SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25 under high stringency conditions.

An isolated TAS2R receptor polypeptide encoded by the polynucleotide, and expression vectors and host cells for expressing the encoded TAS2R receptor are also disclosed.

In an embodiment, the isolated TAS2R receptor polypeptide comprises at least one extracellular domain of a feline TAS2R receptor; at least one transmembrane domain of a feline TAS2R receptor; or at least one intracellular domain of a feline TAS2R receptor, wherein the feline TAS2R receptor comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

In an embodiment, the isolated TAS2R receptor polypeptide comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

Also disclosed herein is a chimeric polypeptide comprising an extracellular domain or a transmembrane region of a feline TAS2R receptor polypeptide linked to a heterologous polypeptide.

In an embodiment, the chimeric polypeptide comprises an extracellular domain of a feline TAS2R receptor polypeptide comprising amino acids 1, 68-84; 146-179; or 249-257 of SEQ ID NO:2; amino acids 1-10, 73-88; 151-186; or 256-264 of SEQ ID NO:4; amino acids 1-8; 72-88; 150-186; or 256-265 of SEQ ID NO:6; amino acids 1-2; 69-87; 151-183; or 253-261 of SEQ ID NO:8; amino acids 1-8; 72-88; 150-187; or 257-265 of SEQ ID NO:10; amino acids 1-6; 72-88; 150-183; or 253-262 of SEQ ID NO:12; amino acids 1; 69-87; 150-181; or 251-260 of SEQ ID NO:14; amino acids 1-8; 69-88; 150-185; or 252-261 of SEQ ID NO:16; amino acids 1-17: 83-98; 161-198; or 268-277 of SEQ ID NO:18; amino acids 1; 69-88; 150-185; or 255-264 of SEQ ID NO:20; amino acids 1-2; 69-87; 149-181; or 251-260 of SEQ ID NO:22; amino acids 1-2; 69-87; 149-181; or 251-259 of SEQ ID NO:24; or amino acids 1-8; 72-88; 150-185; or 254-263 of SEQ ID NO:26; or a transmembrane region of the feline TAS2R receptor polypeptide comprising amino acids 2-22, 47-67, 85-105, 125-145, 180-200, 228-248, or 258-278 of SEQ ID NO:2; amino acids 11-31, 52-72, 89-109, 130-150, 187-207, 235-255, or 265-285 of SEQ ID NO:4; amino acids 9-29, 51-71, 89-109, 129-149, 187-207, 235-255, or 266-286 of SEQ ID NO:6; amino acids 3-23, 48-68, 88-108, 130-150, 184-204, 232-252, or 262-282 of SEQ ID NO:8; amino acids 9-29, 51-71, 89-109, 129-149, 188-208, 236-256, or 266-286 of SEQ ID NO:10; amino acids 7-27, 51-71, 89-109, 129-149, 184-204, 232-252, or 263-283 of SEQ ID NO:12; amino acids 2-22, 48-68, 88-108, 129-149, 182-202, 230-250, or 261-281 of SEQ ID NO:14; amino acids 9-29, 48-68, 89-109, 129-149, 186-206, 231-251, or 262-282 of SEQ ID NO:16; amino acids 18-38, 62-82, 99-119, 140-160, 199-219, 247-267, or 278-298 of SEQ ID NO:18; amino acids 2-22, 48-68, 89-109, 129-149, 186-206, 234-254, or 265-285 of SEQ ID NO:20; amino acids 3-23, 48-68, 88-108, 128-148, 182-202, 230-250, or 261-281 of SEQ ID NO:22; amino acids 3-23, 48-68, 88-108, 128-148, 182-202, 230-250, or 260-280 of SEQ ID NO:24; or amino acids 9-29, 51-71, 89-109, 129-149, 186-206, 233-253, or 264-284 of SEQ ID NO:26; linked to a heterologous polypeptide.

Antibodies and kits for detecting the fTAS2R receptor or the polynucleotide encoding the fTAS2R receptor are also disclosed.

Also disclosed herein are methods for identifying compounds that interact with a fTAS2R receptor.

In an embodiment, the method comprises contacting a fTAS2R receptor herein with a test compound, and detecting interaction between the receptor and the compound.

In an embodiment, the method comprises contacting a fTAS2R receptor with a receptor ligand in the presence or absence of a test compound, and determining whether the test compound modulates binding of the ligand to the receptor or activation of the receptor by the ligand.

In an embodiment, the method comprises contacting a fTAS2R receptor herein with a test compound, and detecting an increase in biological activity of the receptor in the presence of the compound relative to biological activity of the polypeptide in the absence of the compound.

In an embodiment, the method comprises contacting a fTAS2R receptor herein with a test compound, and detecting a decrease in biological activity of the receptor in the presence of the compound relative to biological activity of the polypeptide in the absence of the compound.

These and other advantages, as well as additional inventive features, will be apparent from the following Drawings, Detailed Description, Examples, and Claims.

BRIEF DESCRIPTION OF THE DRAWINGS

FIG. 1 is a sequence alignment displaying the 3rd through the 7th transmembrane (TM) region (transmembrane regions in grey) of several human and feline bitter receptors: human TAS2R16 (SEQ ID NO:30), TAS2R4 (SEQ ID NO:27), TAS2R9 (SEQ ID NO:28), TAS2R10 (SEQ ID NO:29) AND TAS2R38 (SEQ ID NO:31); and feline bitter receptors, TAS2R4 (SEQ ID NO:8), 9 (SEQ ID NO:12), 10 (SEQ ID NO:14), 12 (SEQ ID NO:16), and 38 (SEQ ID NO:18).

FIG. 2 shows a sequence alignment for human TAS2R38 polypeptide (SEQ ID NO:31) and feline TAS2R38 polypeptide (SEQ ID NO:18) determined from sequencing of genomic DNA of five individual cats.

DETAILED DESCRIPTION

A family of novel feline bitter taste receptors, referred to as feline TAS2R (fTAS2R), are disclosed herein. These G-protein coupled receptors (GPCRs) are components of the feline taste transduction pathway, specifically, part of the bitter taste transduction pathway, and are involved in feline taste detection of bitter substances such as 6-n-propylthiouracil, sucrose octaacetate, raffinose undecaacetate, cycloheximide, denatonium, copper glycinate, and quinine Isolated polynucleotides encoding the novel feline bitter taste receptors are also disclosed, as are expression vectors and host cells for expression of the novel feline bitter taste receptors. Methods of expressing and isolating the nucleic acids and encoded polypeptides are also disclosed.

The nucleic acids provide probes for identification of cells in which the nucleic acids are expressed, e.g., taste cells. For example, probes for expression of TAS2R polypeptides can be used to identify taste cells present in foliate, circumvallate, and fungiform papillae. In particular, the TAS2R probes are useful to identify bitter sensing cells and can serve as tools for the generation of anatomical maps that elucidate the relationship between the bitter sensing cells and their projections into the central nervous system. Methods of identifying compounds that bind to the novel feline bitter taste receptors and modulate their activity are disclosed. In the methods, members of the fTAS2R family act as direct or indirect reporter molecules to identify modulators of taste receptor expressing cellular activity. Such compounds that modulate feline bitter taste receptor activity are useful for modulation of feline bitter taste receptor activity. Modulators can be activators, inhibitors, enhancers, agonists, and/or antagonists of the feline bitter receptors. These modulatory compounds can be used in the food and pharmaceutical industries to customize taste of foods or drugs, for example, to decrease the bitter taste of foods or drugs. Thus, the methods disclosed herein are useful for designing formulations of feline food, feline food palatants, feline treats, and feline medications in which aversive compounds are avoided or blocked.

Bitter taste perception is mediated by G protein-coupled receptors (GPCRs) of the taste receptor 2 family (TAS2R). The TAS2R genes encode a family of related seven transmembrane G-protein coupled receptors involved in taste transduction, which interact with a G-protein to mediate taste signal transduction. In particular, TAS2Rs interact in a ligand-specific manner with the G protein Gustducin.

To date, much work has been done to characterize human TAS2Rs (hTAS2Rs). The human genome encodes about 26 functional TAS2Rs that are glycoproteins. All hTAS2Rs share a conserved site for Asn-linked glycosylation within the center of the second extracellular loop. The hTAS2Rs also have the ability to form homo- and hetero-oligomers with other GPCR when expressed in vitro, however at present no evidence exists that TAS2R receptor oligomerization has functional implications.

Bitter taste receptor cells represent a distinct subpopulation of chemosensory cells characterized by the expression of TAS2R genes and completely segregated from those receptor cells devoted to the detection of other taste stimuli. Each bitter taste receptor cell expresses multiple bitter taste receptors, although the extent of co-expression is still a matter of debate.

In addition to their expression in the gustatory system, TAS2Rs are found in non-gustatory tissues. Among these extraoral sites are the respiratory epithelia, gastrointestinal tissues, reproductive organs, and brain. Bitter taste receptors are implicated in differentiation or maturation of sperm in mice. The non-gustatory expression of TAS2Rs is known to be used to regulate digestion and respiration.

Activation of TAS2R receptors in an enteroendocrine cell line (STC-1 cells) results in release of the peptide hormone cholecystokinin (CCK), which can reduce gut motility. Consequently, intake of a potential toxin that activates the TAS2R pathway may decrease the rate at which food passes through the stomach and lower the drive for continued eating. The release of CCK also excites sensory nerve processes of the vagus nerve to carry the signal to the brain, suggesting that regulation of food intake involves both peripheral and central controls. Activation of the TAS2R signaling network may also or alternatively indirectly increase elimination of absorbed toxins from gut epithelium before the toxins can enter circulation since some data suggest that the CCK-secreting enteroendocrine cells are involved in a paracrine signaling system that reduces transfer of toxic substances from the gut into the circulation. Lower in the gut, activation of TAS2R receptors has a different effect. When some bitter-tasting ligands are applied to the colonic epithelium, they induce the secretion of anions, which leads to fluid secretion by the epithelium which may flush out any noxious irritant from the colon.

Solitary chemosensory cells (SCCs) are also present throughout the upper respiratory system and express the entire suite of taste-related signaling molecules, including TAS2R receptors, PLCβ2, gustducin, and the transduction channel TrpM5. The SCCs synapse onto polymodal pain fibers of the trigeminal nerve. Inhalation of a toxin that activates TAS2R receptors of the SCCs will be irritating and evoke trigeminally-mediated reflex changes in respiration. Additionally, the activated trigeminal nerve fibers release peptide modulators that result in local neurogenic inflammation of the respiratory epithelium, activating the immune system in response to the presence of the toxins.

Ligands of a mammalian TAS2R1 can include adhumulone, adlupulone, amarogentin, arborescin, cascarillin, chloramphenicol, cis-isocohumulone, cis-isoloadhumulone, cohumulone, colupulone, dextromethorphan, diphenidol (diphenylthiourea, sulfocarbanilide, sym-diphenylthiourea, or thiocarbanilide), humulon (humulone), isoxanthohumol, lupulon, lupulone, parthenolide, picrotoxinin, sodium cyclamate, sodium thiocyanate, thiamine, trans-isoadhumulone, trans-isocohumulone, trans-isohumulone, xanthohumol, and yohimbine. The mammalian TAS2R1 can be from a human, a rodent, a canine, or a feline. In an embodiment, the mammalian TAS2R1 is a feline TAS2R1.

Ligands of a mammalian TAS2R3 can include chloroquine. The mammalian TAS2R3 can be from a human, a rodent, a canine, or a feline. In an embodiment, the mammalian TAS2R3 is a feline TAS2R3.

Ligands of a mammalian TAS2R4 can include amarogentin, arborescin, artemorin, azathioprine, brucine, campher, chlorpheniramine, colchicine, dapsone, denatonium benzoate, diphenidol, parthenolide, quassin, quinine, and yohimbine. The mammalian TAS2R4 can be from a human, a rodent, a canine, or a feline. In an embodiment, the mammalian TAS2R4 is a feline TAS2R4.

Ligands of a mammalian TAS2R7 can include caffeine, chlorpheniramine, cromolyn, diphenidol, papaverine, and quinine. The mammalian TAS2R7 can be from a human, a rodent, a canine, or a feline. In an embodiment, the mammalian TAS2R7 is a feline TAS2R7.

Ligands of a mammalian TAS2R9 can include ofloxacin, pirenzapin, and procainamid. The mammalian TAS2R9 can be from a human, a rodent, a canine, or a feline. In an embodiment, the mammalian TAS2R9 is a feline TAS2R9.

Ligands of a mammalian TAS2R10 can include (−)-alpha thujone, absinthin, arborescin, arglabin, artemorin, azathioprine, benzoin, caffeine, campher, cascarillin, chloramphenicol, chloroquine, chlorpheniramine, coumarin, cucurbitacin b, cucurbitacin e, cucurbitacins, cycloheximid, cycloheximide, dapsone, denatonium benzoate, dextromethorphan, diphenidol, erythromycin, famotidine, haloperidol, papaverine, parthenolide, picrotoxinin, quassin, quinine, strychnine, and yohimbine. The mammalian TAS2R10 can be from a human, a rodent, a canine, or a feline. In an embodiment, the mammalian TAS2R10 is a feline TAS2R10.

Ligands of a mammalian TAS2R38 can include 6-methyl-2-thiouracil, acetylthiourea, allyl isothiocyanate, caprolactam, chlorpheniramine, dimethylthioformamide, diphenidol, (diphenylthiourea, sulfocarbanilide, sym-diphenylthiourea, thiocarbanilide), ethylene thiourea, n,n-ethylene thiourea, ethylpyrazine, limonin, methimazole, n-ethylthiourea, n-methylthiourea, phenethyl isothiocyanate, phenylthiocarbamide (ptc), propylthiouracil, sinigrin, sodium cyclamate, sodium_thiocyanate, and yohimbine. The mammalian TAS2R38 can be from a human, a rodent, a canine, or a feline. In an embodiment, the mammalian TAS2R38 is a feline TAS2R38.

Ligands of a mammalian TAS2R43 can include acesulfame K, aloin, amarogentin, arborescin, arglabin, aristolochic acid, caffeine, chloramphenicol, cromolyn, denatonium benzoate, diphenidol, falcarindiol, grosheimin (grossheimin), helicin, quinine, and saccharin. The mammalian TAS2R43 can be from a human, a rodent, a canine, or a feline. In an embodiment, the mammalian TAS2R43 is a feline TAS2R43.

Ligands of a mammalian TAS2R44 can include acesulfame K, aloin, aristolochic acid, diphenidol, famotidine, parthenolide, quinine, and saccharin. The mammalian TAS2R44 can be from a human, a rodent, a canine, or a feline. In an embodiment, the mammalian TAS2R44 is a feline TAS2R44.

The human bitter taste receptors, hTAS2R2, hTAS2R41, hTAS2R42, hTAS2R45, hTAS2R48, and hTAS2R60 are still considered orphan GPCRs since ligands have not yet been identified for these receptors.

Until recently, hTAS2R2 was annotated as a pseudogene due to a two base deletion at codon 160 found in sequences collected from 10 human populations (Karitiana, Surui, Waorani Indians from South America, Russians from Eastern Europe, Druze from the Middle East, Atayal, Chinese, Japanese from Eastern Asia, and Khmers and Melanesians from Southeast Asia) and from GenBank resources. hTAS2R2 has been found to be polymorphic with respect to that deletion, with the intact gene found in the Adygei (Eastern European), Mbuti (African Pygmies), and Biaka (African Pygmies) (Go Y et al., Genetics May 1, 2005, 170 (1): 313-326).

Human TAS2R (hTAS2R) gene and pseudogene nucleotide sequences were used as references to identify, via a bioinformatics approach, previously unknown feline TAS2R (fTAS2R) genes. Subsequently, isolated feline genomic DNA was used to clone the fTAS2R genes. The nucleotide sequence of the cloned fTAS2R genes of several felines was then determined by sequencing, e.g., Sanger sequencing, and used to establish a consensus nucleotide sequence for the gene, and to identify any variant sites in the sequence.

An isolated polynucleotide encoding a fTAS2R receptor is disclosed. The isolated polynucleotide can comprise the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25; a nucleotide sequence encoding the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; a nucleotide sequence substantially complementary to the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25; or a nucleotide sequence that hybridizes to the complement of the polynucleotide having SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25 under high stringency conditions.

Further disclosed is a polynucleotide comprising a sequence having at least 90%, at least 95%, at least 97%, at least 98%, at least 99% homology with SEQ ID NO:1, 3, 5, 7, 9, 11, 13, 15, 17, 19, 21, 23, 25, or the complement of SEQ ID NO:1, 3, 5, 7, 9, 11, 13, 15, 17, 19, 21, 23, or 25.

A single nucleotide polymorphism in the nucleic acid sequence encoding fTAS2R38 was identified at nucleotide 220 from sequencing amplified feline genomic DNA from multiple subjects. The two alleles observed at the nucleotide 220 were G and A. The G220A nucleic acid variation corresponds to an amino acid variation D74N in the fTAS2R38 protein sequence.

In another aspect, an isolated fTAS2R receptor polypeptide is disclosed.

In an embodiment, the isolated fTAS2R polypeptide is encoded by a polynucleotide disclosed herein.

In an embodiment, the isolated fTAS2R polypeptide can comprise the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or an amino acid sequence having at least 90%, at least 95%, at least 97%, at least 98%, at least 99% homology with the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

Sensory GPCRs, such as the TAS2R bitter taste receptors, have a domain structure including an "N-terminal domain"; "extracellular domains"; a "transmembrane domain" comprising seven transmembrane regions, cytoplasmic, and extracellular loops; "cytoplasmic domains"; and a "C-terminal domain". These domains can be structurally identified using methods known in the art, such as sequence analysis programs that identify hydrophobic and hydrophilic domains. Such domains are useful for making chimeric proteins and for in vitro assays disclosed herein, e.g., ligand binding assays.

The term "extracellular domains" refers to the domains of TAS2R polypeptides that protrude from the cellular membrane and are exposed to the extracellular face of the cell. Such domains would include the "N terminal domain" that is exposed to the extracellular face of the cell, as well as the extracellular loops of the transmembrane domain that are exposed to the extracellular face of the cell, i. e., the loops between transmembrane regions 2 and 3, and between transmembrane regions 4 and 5.

The "N terminal domain" region starts at the N-terminus and extends to a region close to the start of the transmembrane domain. These extracellular domains are useful for in vitro ligand binding assays, both soluble and solid phase.

The "transmembrane domain," which comprises the seven transmembrane regions, refers to the domain of TAS2R polypeptides that lies within the plasma membrane, and may also include the corresponding cytoplasmic (intracellular) and extracellular loops, also referred to as transmembrane domain "regions." Transmembrane regions can also bind ligand either in combination with the extracellular domain or alone, and are therefore also useful for in vitro ligand binding assays.

The seven transmembrane regions and extracellular and cytoplasmic loops can be identified using standard methods known in the art. For example, transmembrane regions of the fTAS2R proteins can be identified using software, TOPCONS, available on the internet from the Stockholm Bioinformatics Center, Stockholm University (Andreas Bernsel, et al. (2009) Nucleic Acids Research 37 (Webserver issue), W465-8). The seven transmembrane regions and extracellular and cytoplasmic loops of the fTAS2R identified by TOPCONS are shown in the following table:

TABLE 1

TOPCONS prediction of seven transmembrane regions, extracellular loops, and intracellular loops fTAS2R1 (SEQ ID NO: 2)

Transmembrane domains: 1: 2-22, 2: 47-67, 3: 85-105, 4: 125-145, 5: 180-200, 6: 228-248, 7: 258-278
Extracellular domain: 1, 68-84; 146-179; 249-257
Intracellular domain: 23-46; 106-124; 201-227; 279-298
fTAS2R2 (SEQ ID NO: 4)

Transmembrane domains: 1: 11-31, 2: 52-72, 3: 89-109, 4: 130-150, 5: 187-207, 6: 235-255, 7: 265-285
Extracellular domain: 1-10, 73-88; 151-186; 256-264
Intracellular domain: 32-51; 110-129; 208-234; 286-304
fTAS2R3 (SEQ ID NO: 6)

Transmembrane domains: 1: 9-29, 2: 51-71, 3: 89-109, 4: 129-149, 5: 187-207, 6: 235-255, 7: 266-286
Extracellular domain: 1-8; 72-88; 150-186; 256-265
Intracellular domain: 30-50; 110-128; 208-234; 287-316
fTAS2R4 (SEQ ID NO: 8)

Transmembrane domains: 1: 3-23, 2: 48-68, 3: 88-108, 4: 130-150, 5: 184-204, 6: 232-252, 7: 262-282
Extracellular domain: 1-2; 69-87; 151-183; 253-261
Intracellular domain: 24-47; 109-129; 205-231; 283-306
fTAS2R7 (SEQ ID NO: 10)

Transmembrane domains: 1: 9-29, 2: 51-71, 3: 89-109, 4: 129-149, 5: 188-208, 6: 236-256, 7: 266-286
Extracellular domain: 1-8; 72-88; 150-187; 257-265
Intracellular domain: 30-50; 110-128; 209-235; 287-311
fTAS2R9 (SEQ ID NO: 12)

Transmembrane domains: 1: 7-27, 2: 51-71, 3: 89-109, 4: 129-149, 5: 184-204, 6: 232-252, 7: 263-283
Extracellular domain: 1-6; 72-88; 150-183; 253-262
Intracellular domain: 28-50; 110-128; 205-231; 284-337
fTAS2R10 (SEQ ID NO: 14)

Transmembrane domains: 1: 2-22, 2: 48-68, 3: 88-108, 4: 129-149, 5: 182-202, 6: 230-250, 7: 261-281
Extracellular domain: 1; 69-87; 150-181; 251-260
Intracellular domain: 23-48; 109-128; 203-229; 282-300
fTAS2R12 (SEQ ID NO: 16)

Transmembrane domains: 1: 9-29, 2: 48-68, 3: 89-109, 4: 129-149, 5: 186-206, 6: 231-251, 7: 262-282
Extracellular domain: 1-8; 69-88; 150-185; 252-261
Intracellular domain: 30-47; 110-128; 207-230; 283-309
fTAS2R38 (SEQ ID NO: 18)

Transmembrane domains: 1: 18-38, 2: 62-82, 3: 99-119, 4: 140-160, 5: 199-219, 6: 247-267, 7: 278-298
Extracellular domain: 1-17; 83-98; 161-198; 268-277
Intracellular domain: 39-61; 120-139; 220-246; 299-334
fTAS2R42 (SEQ ID NO: 20)

Transmembrane domains: 1: 2-22, 2: 48-68, 3: 89-109, 4: 129-149, 5: 186-206, 6: 234-254, 7: 265-285
Extracellular domain: 1; 69-88; 150-185; 255-264
Intracellular domain: 23-47; 110-128; 207-233; 286-322
fTAS2R43 (SEQ ID NO: 22)

Transmembrane domains: 1: 3-23, 2: 48-68, 3: 88-108, 4: 128-148, 5: 182-202, 6: 230-250, 7: 261-281
Extracellular domain: 1-2; 69-87; 149-181; 251-260
Intracellular domain: 24-47; 109-127; 203-229; 282-299

TABLE 1-continued

TOPCONS prediction of seven transmembrane regions, extracellular loops, and intracellular loops fTAS2R44 (SEQ ID NO: 24)

Transmembrane domains: 1: 3-23, 2: 48-68, 3: 88-108, 4: 128-148, 5: 182-202, 6: 230-250, 7: 260-280
Extracellular domain: 1-2; 69-87; 149-181; 251-259
Intracellular domain: 24-47; 109-127; 203-229; 281-308
fTAS2R67 (SEQ ID NO: 26)

Transmembrane domains: 1: 9-29, 2: 51-71, 3: 89-109, 4: 129-149, 5: 186-206, 6: 233-253, 7: 264-284
Extracellular domain: 1-8; 72-88; 150-185; 254-263
Intracellular domain: 30-50; 110-128; 207-232; 285-312

Alternative predictions of the transmembrane regions and extracellular and cytoplasmic loops of the fTAS2R proteins can be generated using different software also available on the internet from the Stockholm Bioinformatics Center, including SCAMPI (Andreas Bernsel, et al. (2008) Proc. Natl. Acad. Sci. USA. 105, 7177-7181.); PRODIV (Håkan Viklund and Arne Elofsson (2004) Protein Science 13, 1908-1917), and OCTAPUS (Håkan Viklund and Arne Elofsson (2008) Bioinformatics. 24, 1662-1668.) Additional methods known in the art to predict the structural regions include hydropathy prediction methods of Goldman-Engleman-Steitz, or Kyte-Doolittle (J. Mol. Biol. 157: 105-132 (1982), or Hopp-Woods. Secondary structure prediction methods include Garnier-Robson, or Deléage & Roux or Chou-Fasman. As known in the art, the various available algorithms may predict slightly different boundaries for transmembrane regions based on the amino acid sequence.

The term "transmembrane region" as used herein denotes a three-dimensional protein structure which is thermodynamically stable in a membrane, e.g., a single transmembrane alpha helix or a transmembrane beta barrel.

"Cytoplasmic domains" refers to the domains of TAS2R proteins that face the inside of the cell, e. g., the "C terminal domain" and the intracellular loops of the transmembrane domain, e. g., the intracellular loops between transmembrane regions 1 and 2, the intracellular loops between transmembrane regions 3 and 4, and the intracellular loops between transmembrane regions 5 and 6.

"C terminal domain" refers to the region that spans the end of the last transmembrane domain and the C-terminus of the protein, and which is normally located within the cytoplasm.

In an embodiment, the isolated TAS2R receptor polypeptide can comprise at least one extracellular domain of a feline TAS2R receptor; at least one transmembrane domain of a feline TAS2R receptor; or at least one intracellular domain of a feline TAS2R receptor, wherein the feline TAS2R receptor comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or an amino acid sequence having at least 90% homology, specifically at least 95% homology, more specifically at least 97% homology with the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

The extracellular domain of the fTAS2R polypeptide can comprise amino acids 1, 68-84; 146-179; or 249-257 of SEQ ID NO:2; amino acids 1-10, 73-88; 151-186; or 256-264 of SEQ ID NO:4; amino acids 1-8; 72-88; 150-186; or 256-265 of SEQ ID NO:6; amino acids 1-2; 69-87; 151-183; or 253-261 of SEQ ID NO:8; amino acids 1-8; 72-88; 150-187; or 257-265 of SEQ ID NO:10; amino acids 1-6; 72-88; 150-183; or 253-262 of SEQ ID NO:12; amino acids 1; 69-87; 150-181; or 251-260 of SEQ ID NO:14; amino acids 1-8; 69-88; 150-185; or 252-261 of SEQ ID NO:16; amino acids 1-17: 83-98; 161-198; or 268-277 of SEQ ID NO:18; amino acids 1; 69-88; 150-185; or 255-264 of SEQ ID NO:20; amino acids 1-2; 69-87; 149-181; or 251-260 of SEQ ID NO:22; amino acids 1-2; 69-87; 149-181; or 251-259 of SEQ ID NO:24; or amino acids 1-8; 72-88; 150-185; or 254-263 of SEQ ID NO:26.

The transmembrane domain of the fTAS2R polypeptide can comprise amino acids 2-22, 47-67, 85-105, 125-145, 180-200, 228-248, or 258-278 of SEQ ID NO:2; amino acids 11-31, 52-72, 89-109, 130-150, 187-207, 235-255, or 265-285 of SEQ ID NO:4; amino acids 9-29, 51-71, 89-109, 129-149, 187-207, 235-255, or 266-286 of SEQ ID NO:6; amino acids 3-23, 48-68, 88-108, 130-150, 184-204, 232-252, or 262-282 of SEQ ID NO:8; amino acids 9-29, 51-71, 89-109, 129-149, 188-208, 236-256, or 266-286 of SEQ ID NO:10; amino acids 7-27, 51-71, 89-109, 129-149, 184-204, 232-252, or 263-283 of SEQ ID NO:12; amino acids 2-22, 48-68, 88-108, 129-149, 182-202, 230-250, or 261-281 of SEQ ID NO:14; amino acids 9-29, 48-68, 89-109, 129-149, 186-206, 231-251, or 262-282 of SEQ ID NO:16; amino acids 18-38, 62-82, 99-119, 140-160, 199-219, 247-267, or 278-298 of SEQ ID NO:18; amino acids 2-22, 48-68, 89-109, 129-149, 186-206, 234-254, or 265-285 of SEQ ID NO:20; amino acids 3-23, 48-68, 88-108, 128-148, 182-202, 230-250, or 261-281 of SEQ ID NO:22; amino acids 3-23, 48-68, 88-108, 128-148, 182-202, 230-250, or 260-280 of SEQ ID NO:24; or amino acids 9-29, 51-71, 89-109, 129-149, 186-206, 233-253, or 264-284 of SEQ ID NO:26.

The intracellular domain of the fTAS2R polypeptide can comprise amino acids 23-46; 106-124; 201-227; or 279-298 of SEQ ID NO:2; amino acids 32-51; 110-129; 208-234; or 286-304 of SEQ ID NO:4; amino acids 30-50; 110-128; 208-234; or 287-316 of SEQ ID NO:6; amino acids 24-47; 109-129; 205-231; or 283-306 of SEQ ID NO:8; amino acids 30-50; 110-128; 209-235; or 287-311 of SEQ ID NO:10; amino acids 28-50; 110-128; 205-231; or 284-337 of SEQ ID NO:12; amino acids 23-48; 109-128; 203-229; or 282-300 of SEQ ID NO:14; amino acids 30-47; 110-128; 207-230; or 283-309 of SEQ ID NO:16; amino acids 39-61; 120-139; 220-246; or 299-334 of SEQ ID NO:18; amino acids 23-47; 110-128; 207-233; or 286-322 of SEQ ID NO:20; amino acids 24-47; 109-127; 203-229; or 282-299 of SEQ ID NO:22; amino acids 24-47; 109-127; 203-229; or 281-308 of SEQ ID NO:24; or amino acids 30-50; 110-128; 207-232; or 285-312 of SEQ ID NO:26.

Also disclosed is a polynucleotide encoding the polypeptide comprising at least one extracellular domain of a feline TAS2R receptor; at least one transmembrane domain of a feline TAS2R receptor; or at least one intracellular domain of a feline TAS2R receptor.

In another aspect, a chimeric polypeptide comprising an extracellular domain or a transmembrane region of a feline TAS2R receptor polypeptide linked to a heterologous polypeptide is disclosed. The extracellular domain or the transmembrane region of the feline TAS2R receptor polypeptide can be any of those disclosed herein.

The heterologous polypeptide can be any suitable polypeptide known in the art. The heterologous polypeptide can be, for example, a sequence to determine cellular localization and expression, to permit proper folding of the chimeric polypeptide in an expression system, and/or to facilitate isolation of the chimeric polypeptide. The heterologous polypeptide can be linked to the amino terminal end or the carboxy terminal end of the fTAS2R sequence. For example, the heterologous polypeptide can be the first 45 amino acids of rat somatostatin, the FLAG® tag, a 6× histidine (his) tag, MYC, a fluorescent protein tag, V5, and/or glutathione S-transferase (GST). When the heterologous polypeptide is the first 45 amino acids of rat somatostatin, it is typically placed at the amino terminal end of the chimeric polypeptide to permit membrane targeting. When the heterologous polypeptide is a tag to permit easier isolation of the chimeric polypeptide, e.g., a 6× histidine tag, it can be placed at the amino terminus of the chimeric polypeptide. Determination of a suitable location for the heterologous polypeptide in the chimeric polypeptide relative to the amino end or the carboxy end of the fTAS2R sequence to obtain a particular functional aspect of the heterologous polypeptide on the chimeric polypeptide can be made by one of skill in the art.

Also disclosed is a polynucleotide encoding the chimeric polypeptide.

The terms "polypeptide," "peptide", and "protein" are used interchangeably herein to refer to a molecule formed from the linking, in a defined order, of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis, or enzymatic synthesis. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission.

Unless otherwise indicated, a particular polypeptide sequence also implicitly encompasses conservatively modified variants thereof. A conservative amino acid substitution in a polypeptide sequence includes the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys);

Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. One of skill in the art can readily determine regions of the molecule of interest that can tolerate change by reference to Hopp/Woods and Kyte-Doolittle plots.

Macromolecular structures such as polypeptide structures can be described in terms of various levels of organization. "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of .beta.-sheet and .alpha.-helices. "Tertiary structure" refers to the complete three dimensional structure of a polypeptide monomer. "Quaternary structure" refers to the three dimensional structure formed by the noncovalent association of independent tertiary units.

The term "chimeric polypeptide" refers to a molecule, which does not occur in isolated form in nature, in which all or a portion of an fTAS2R polypeptide sequence is part of the linear chimeric polypeptide sequence. The portion of an fTAS2R polypeptide sequence can be the amino acid sequence of one or more domains of the complete fTAS2R polypeptide. For example, the portion can be an extracellular domain of a fTAS2R polypeptide. The chimeric polypeptide can be made by any method known in the art. For example, the chimeric polypeptide can be made by a recombinant expression system or can be synthesized.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome. Purity and homogeneity are typically determined using analytical chemistry techniques, for example polyacrylamide gel electrophoresis or high performance liquid chromatography. A protein that is the predominant species present in a preparation is substantially purified. In particular, an isolated TAS2R nucleic acid is separated from open reading frames that flank the TAS2R gene and encode proteins other than a TAS2R. In some embodiments, the term "purified" means that the nucleic acid or protein is at least 85% pure, specifically at least 90% pure, more specifically at least 95% pure, or yet more specifically at least 99% pure.

The term "nucleic acid" or "polynucleotide" includes DNA molecules and RNA molecules. A polynucleotide may be single-stranded or double-stranded. Polynucleotides can contain known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs). A polynucleotide can be obtained by a suitable method known in the art, including isolation from natural sources, chemical synthesis, or enzymatic synthesis. Nucleotides may be referred to by their commonly accepted single-letter codes.

Unless otherwise indicated, a particular nucleic acid sequence also implicitly encompasses conservatively modified variants thereof (e.g. degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Homology" refers to the percent identity between two polynucleotide or two polypeptide moieties. Two DNA, or two polypeptide sequences are "substantially homologous" to each other when the sequences exhibit at least about 50%, specifically at least about 75%, more specifically at least about 80%-85%, at least about 90%, and most specifically at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN (Dayhoff, M. O. in Atlas of Protein Sequence and Structure M. O. Dayhoff ed., 5 Suppl. 3:353-358, National Biomedical Research Foundation, Washington, D.C.), which adapts the local homology algorithm of Smith and Waterman 1981 Advances in Appl Math 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, nucleotide homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. Molecular Cloning: A Laboratory Manual (2d ed., Cold Spring Harbor Laboratory Press, Cold Spring Harbor, N.Y. (1989)).

The term "recombinant" can be used to describe a nucleic acid molecule and refers to a polynucleotide of genomic, RNA, DNA, cDNA, viral, semisynthetic, or synthetic origin which, by virtue of its origin or manipulation is not associated with all or a portion of the polynucleotide with which it is associated in nature.

The term "recombinant" as used with respect to a protein or polypeptide can refer to a polypeptide produced by expression of a recombinant polynucleotide. In general, the gene of interest is cloned and then expressed in transformed organisms, by a method known in the art. The host organism expresses the foreign gene to produce the protein under expression conditions. Disclosed herein is an expression vector comprising a polynucleotide encoding a feline TAS2R polypeptide disclosed herein. In an embodiment, the recombinant vector comprises a polynucleotide consisting of SEQ ID NO:1, 3, 5, 7, 9, 11, 13, 15, 17, 19, 21, 23, or 25; a polynucleotide consisting of the complement of SEQ ID NO:1, 3, 5, 7, 9, 11, 13, 15, 17, 19, 21, 23, or 25; or a polynucleotide consisting of a sequence having at least 90%, at least 95%, at least 97%, at least 98%, at least 99% homology with SEQ ID NO:1, 3, 5, 7, 9, 11, 13, 15, 17, 19, 21, 23, 25, or the complement of SEQ ID NO:1, 3, 5, 7, 9, 11, 13, 15, 17, 19, 21, 23, or 25. Also disclosed is an expression vector comprising a polynucleotide encoding a chimeric polypeptide disclosed herein.

The term "vector" means a nucleic acid sequence to express a target gene in a host cell. Examples include a plasmid vector, a cosmid vector, a bacteriophage vector, and a viral vector. Examples of viral vectors include a bacteriophage vector, an adenovirus vector, a retrovirus vector, and an adeno-associated virus vector.

For example, the vector may be an expression vector including a membrane targeting or secretion signaling sequence or a leader sequence, in addition to an expression control element such as promoter, operator, initiation codon, termination codon, polyadenylation signal, and enhancer. The vector may be manufactured in various ways known in the art depending on the purpose. An expression vector may include a selection marker for selecting a host cell containing the vector. Further, a replicable expression vector may include an origin of replication.

The term "recombinant vector" or "expression vector" means a vector operably linked to a heterologous nucleotide sequence for the purpose of expression, production, and isolation of the heterologous nucleotide sequence. The heterologous nucleotide sequence can be a nucleotide sequence encoding all or part of a fTAS2R receptor or a chimeric polypeptide disclosed herein.

The recombinant vector may be constructed for use in prokaryotic or eukaryotic host cells. For example, when a prokaryotic cell is used as a host cell, the expression vector used generally includes a strong promoter capable of initiating transcription (for example, pLλ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example f1 origin of replication, SV40 origin of replication, pMB1 origin of replication, adeno origin of replication, AAV origin of replication, or BBV origin of replication, but is not limited thereto. A promoter in an expression vector for a eukaryotic host cell may be a promoter derived from the genomes of mammalian cells (for example, a metallothionein promoter or an EF-1 alpha promoter) or a promoter derived from mammalian viruses (for example, an adenovirus late promoter, a vaccinia virus 7.5K promoter, a Sindbis promoter, a SV40 promoter, a cytomegalovirus promoter, and a tk promoter of HSV). A transcription termination sequence in an expression vector for a eukaryotic host cell may be, in general, a polyadenylation sequence.

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

Further disclosed is a host cell comprising an expression vector or a polynucleotide disclosed herein. A suitable host cell can be transformed with at least one of the recombinant vectors or at least one polynucleotide disclosed herein, for example a polynucleotide consisting of SEQ ID NO:1, 3, 5, 7, 9, 11, 13, 15, 17, 19, 21, 23, or 25.

The host cell of the vector may be any cell that can be practically utilized by the expression vector. For example, the host cell may be a higher eukaryotic cell, such as a mammalian cell, or a lower eukaryotic cell, such as a yeast cell. Further, the host cell may be a prokaryotic cell, such as a bacterial cell. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*; or an intestinal bacterium, such as *Salmonella typhimurium, Serratia marcescens*, and various *Pseudomonas* species. A eukaryotic host cell may be a yeast (e.g., *Saccharomyces cerevisiae*), an insect cell, a plant cell, or an animal cell, for example, mouse Sp2/0, CHO (Chinese hamster ovary) K1, CHO DG44, PER.C6, W138, BHK, COS-7, 293, HepG2, Huh7, 3T3, RIN, HeLa, HEK-293, or a MDCK cell line.

The polynucleotide or recombinant vector including the polynucleotide may be transferred into the host cell using a method known in the art. For example, when a prokaryotic cell is used as the host cell, the transfer may be performed using a CaCl$_2$ method or an electroporation method, and when a eukaryotic cell is used as the host cell, the transfer may be performed by microinjection, calcium phosphate precipitation, electroporation, liposome-mediated transfection, LIPOFECTAMINE® (Life Technologies Corporation) transfection, or gene bombardment, but is not limited thereto.

After the expression vector is introduced into the cells, the transfected cells can be cultured under conditions favoring expression of the fTAS2R. The fTAS2R can be recovered from the culture using standard techniques known in the art.

Antibodies to the fTAS2R receptors and the chimeric polypeptides are also disclosed.

An "anti-TAS2R" or a "TAS2R" antibody is an antibody or antibody fragment that specifically binds a polypeptide encoded by a TAS2R gene, cDNA, or a subsequence thereof.

"Antibody" refers to a polypeptide that specifically binds and recognizes an antigen. The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains; these two are also inter-connected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR) or Joining (J) regions (JH or JL in heavy and light chains respectively). Each VH and VL is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

The term "antigen-binding portion" or "antigen-binding fragment" of an antibody, as used herein, refers to one or more fragments of an antibody that retain the ability to specifically bind to an antigen. It has been shown that certain fragments of a full-length antibody can perform the antigen-binding function of an antibody. Examples of binding fragments denoted as an antigen-binding portion or fragment of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment (Ward et al. (1989) Nature 341, 544-546), which consists of a VH domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions are paired to form monovalent molecules (such a single chain cognate of an immunoglobulin fragment is known as a single chain Fv (scFv). Such single chain antibodies are also encompassed within the term "antibody fragment." Antibody fragments are obtained using conventional techniques known to those with skill in the art, and the fragments are screened for utility in the same general manner as are intact antibodies. Antigen-binding fragments can be produced by recombinant DNA techniques, or by enzymatic or chemical cleavage of intact immunoglobulins.

The term "monoclonal antibody" means an antibody obtained from a population of substantially homogeneous antibodies, i.e., the individual antibodies comprising the population are identical except for possible naturally occurring mutations that may be present in minor amounts. In some embodiments, the term "monoclonal antibody" refers to an antibody derived from a single cell clone.

For preparation of monoclonal or polyclonal antibodies, any technique known in the art can be used. Techniques for the production of single chain antibodies (U.S. Pat. No. 4,946,778) can be adapted to produce antibodies to polypeptides disclosed herein. Also, transgenic mice, or other organisms such as other mammals, may be used to express humanized antibodies. Alternatively, phage display technology can be used to identify antibodies and heteromeric Fab fragments that specifically bind to selected antigens.

Methods of production of polyclonal antibodies are known to those of skill in the art. For example, inbred mice (e.g., BALB/C mice) or rabbits are immunized with the fTAS2R, or fragment thereof, using a standard adjuvant, such as Freund's adjuvant, and a standard immunization protocol. The animal's immune response to the immunogen preparation is monitored by taking test bleeds and determining the titer of reactivity to the fTAS2R. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., Science 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-TAS2R proteins, or even other TAS2R family members or other related proteins from other organisms, using a competitive binding immunoassay. Specific polyclonal antisera and monoclonal antibodies will usually bind with a $K_d$ of at least about 0.1 mM, more usually at least about 1 µM, specifically at least about 0.1 µM or better, and more specifically 0.01 µM or better.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a fTAS2R can be selected to obtain only those polyclonal antibodies that are specifically immunoreactive with the fTAS2R protein or an immunogenic portion thereof and not with other proteins, except for orthologs or polymorphic variants and alleles of the TAS2R protein. This selection may be achieved by subtracting out antibodies that cross-react with TAS2R molecules from other species or other TAS2R molecules. Antibodies can also be selected that recognize only fTAS2R GPCR family members but not other GPCRs. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988)), for a description of immunoassay formats and conditions that can be used to determine specific immunoreactivity). Typically a specific or selective reaction will be at least twice background signal or noise and more typically more than 10 to 100 times background.

Immunoassays can be used to detect, qualitatively or quantitatively, a fTAS2R, e.g., to identify taste receptor cells, especially bitter taste receptor cells, and variants of TAS2R family members.

The anti-fTAS2R antibodies can also be used to isolate feline taste cells from a mixed population of cells obtained from a feline. In an embodiment, isolation of the feline taste cells bound to the anti-fTAS2R antibody can be achieved by flow cytometry. Other methods known in the art can also be used.

Herein a "tastant" means a ligand that can bind to a specific TAS2R receptor or set of receptors. Means to infect/express the nucleic acids and vectors, either individually or as libraries, are well known in the art. A variety of individual cell, organ, or whole animal parameters can be measured by a variety of means. The disclosed fTAS2R sequences can be expressed, for example, in animal taste tissues by delivery with a vector, e.g., adenovirus expression vector.

As known in the art, taste behavior can be determined in a short term assay which directly measures taste preferences by counting licking responses of an animal, e.g., a mouse, using a multi-channel gustometer (e.g., the Davis MS160-Mouse gustometer, DiLog instruments, Tallahassee, Fla.). The mean rate that a mouse will lick a tastant relative to their sampling of an appropriate control (ratio defined as lick rate relative to control) indicates whether the stimulus is appetitive, neutral or aversive. In addition, the change in intake of a palatable stimulus can be evaluated in the presence of the test stimulus to assess enhancement or suppression of the palatable stimulus.

In a further embodiment, animals can be trained to discriminate qualitatively distinct stimuli using operant testing methods known in the art. These animals can then be used to determine qualitative similarity between two stimuli, regardless of palatability or preference.

Alternatively, noninvasive methods such as positron emission tomography (PET) or electroencephalography may be used to monitor neural activity in these preparations. Such preparations may also be used to evaluate the impact of various factors such as age, experience or nutritional state on neural activity elicited by stimuli identified in cell-based experiments to modify receptor function.

Also provided are kits comprising at least one composition, polypeptide, or nucleic acid disclosed herein, optionally contained in a single vial, and may optionally include, e.g., instructions for use in detecting a fTAS2R receptor or a polynucleotide encoding a fTAS2R receptor.

In an embodiment, the kit comprises at least one anti-TAS2R antibody disclosed herein and reagents for detecting a complex between the antibody and the TAS2R antigen. For example, the kit can include a buffer that enables binding reaction between the antibody and the TAS2R antigen in a biological sample, or components for producing the buffer.

The activity of TAS2R polypeptides can be assessed using a variety of in vitro and in vivo assays to determine functional, chemical, and physical effects, e.g., measuring ligand binding (e.g., radioactive ligand binding), second messengers (e.g., cAMP, cGMP, IP3, DAG, or $Ca^{2+}$), ion flux, phosphorylation levels, transcription levels, neurotransmitter levels, and the like. Furthermore, such assays can be used to test for inhibitors and activators of TAS2R family members. Such modulators of taste transduction activity are useful for customizing taste, for example to modify the detection of bitter tastes.

The TAS2R protein of the assay will typically be selected from a polypeptide having a sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; a conservatively modified variant of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26; or a sequence that is at least 90%, at least 95%, at least 97%, at least 98%, at least 99% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

In some embodiments, the polypeptide of the assays will comprise a domain of a TAS2R protein, such as an extracellular domain, transmembrane region, transmembrane domain, cytoplasmic domain, ligand binding domain, subunit association domain, active site, and the like. Either the TAS2R protein or a domain thereof can be covalently linked to a heterologous protein to create a chimeric protein used in the assays described herein.

Modulators of TAS2R receptor activity are tested using TAS2R polypeptides as described above, either recombinant or naturally occurring. The protein can be isolated, expressed in a cell, expressed in a membrane derived from a cell, expressed in tissue or in an animal, either recombinant or naturally occurring. For example, transformed cells or membranes can be used. Modulation is tested using one of the in vitro or in vivo assays described herein. Taste transduction can also be examined in vitro with soluble or solid state reactions, using a full-length TAS2R-GPCR or a chimeric molecule such as an extracellular domain or transmembrane region, or combination thereof, of a TAS2R receptor covalently linked to a heterologous signal transduction domain, or a heterologous extracellular domain and/or transmembrane region covalently linked to the transmembrane and/or cytoplasmic domain of a TAS2R receptor. Furthermore, ligand-binding domains of the protein of interest can be used in vitro in soluble or solid state reactions to assay for ligand binding. In numerous embodiments, a chimeric receptor will be made that comprises all or part of a TAS2R polypeptide as well an additional sequence that facilitates the localization of the TAS2R to the membrane, such as rhodopsin, e.g., an N-terminal fragment of a rhodopsin protein.

Ligand binding to a TAS2R protein, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index), hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-G protein complex. In the presence of GTP, release of the alpha subunit of the G protein from the other two G protein subunits serves as a criterion of activation.

In some embodiments, TAS2R-Gustducin interactions are monitored as a function of TAS2R receptor activation. Ligand dependent coupling of TAS2R receptors with Gustducin can be used as a marker to identify modifiers of any member of the TAS2R family.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

In an embodiment, a TAS2R polypeptide is expressed in a eukaryotic cell as a chimeric receptor with a heterologous, chaperone sequence that facilitates its maturation, targeting through the secretory pathway or membrane localization. In a preferred embodiment, the heterologous sequence is a rhodopsin sequence, such as an N-terminal fragment of a rhodopsin. Such chimeric TAS2R receptors can be expressed in any eukaryotic cell, such as ATCC #CRL-11268 cells. Preferably, the cells comprise a functional G protein, e.g., G[alpha]15, that is capable of coupling the chimeric receptor to an intracellular signaling pathway or to a signaling protein such as phospholipase Cβ. Activation of such chimeric receptors in such cells can be detected using any standard method, such as by detecting changes in intracellular calcium by detecting FURA-2 dependent fluorescence in the cell.

Activated GPCR proteins become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR proteins. For example, compounds that modulate the duration a taste receptor stays active would be useful as a means of prolonging a desired taste or cutting off an unpleasant one.

Samples or assays that are treated with a potential TAS2R protein inhibitor or activator are compared to control samples without the test compound, to examine the extent of modulation. Such assays may be carried out in the presence of a bitter tastant that is known to activate the particular receptor, and modulation of the bitter-tastant-dependent activation monitored. Control samples (untreated with activators or inhibitors) are assigned a relative TAS2R activity value of 100. Inhibition of a TAS2R protein is achieved when the TAS2R activity value relative to the control is about 90%, optionally 50%, optionally 25-0%. Activation of a TAS2R protein is achieved when the TAS2R activity value relative to the control is 110%, optionally 150%, 200-500%, or 1000-2000%.

Changes in ion flux may be assessed by determining changes in polarization (i.e., electrical potential) of the cell or membrane expressing a TAS2R protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode. Whole cell currents are conveniently determined using standard methodology known in the art. Other known assays include: radio labeled ion flux assays and fluorescence assays using voltage-sensitive dyes. Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides disclosed herein. When the functional consequences are determined using intact cells or animals, one can also measure a variety of effects such as transmitter release, hormone release, transcriptional changes to both known and uncharacterized genetic markers (e.g., Northern blots), changes in cell metabolism such as cell growth or pH changes, and changes in intracellular second messengers such as $Ca^{2+}$, IP3, cGMP, or cAMP.

In an embodiment, assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Ion-sensitive indicators and voltage probes that may be employed are commercially available from a variety of sources. For G-protein coupled receptors, promiscuous G-proteins such as Gα15 and Gα16 can be used in the assay of choice. Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, Nature 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., Proc. Natl. Acad. Sci. U.S.A. 88:9868-9872 (1991) and Dhallan et al., Nature 347: 184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In an embodiment, TAS2R protein activity is measured by expressing a TAS2R gene in a heterologous cell with a promiscuous G-protein that links the receptor to a phospholipase C signal transduction pathway (see Offermanns & Simon, J. Biol. Chem. 270:15175-15180 (1995)). Optionally the cell line is a eukaryotic cell line which does not naturally express TAS2R genes and the promiscuous G-protein is G$\alpha$15 (Offermanns & Simon, supra). Modulation of taste transduction is assayed by measuring changes in intracellular $Ca^{2+}$ levels, which change in response to modulation of the TAS2R signal transduction pathway via administration of a molecule that associates with a TAS2R protein. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, J. Biol. Chem. 270: 15175-15180 (1995) may be used to determine the level of cAMP. Also, the method described in Felley-Bosco et al., Am. J. Resp. Cell and Mol. Biol. 11:159-164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436, 128, herein incorporated by reference. Briefly, the assay involves labeling of cells with 3H-myoinositol for 48 or more hours. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing a TAS2R protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using Northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

The compounds tested as modulators of a TAS2R family member can be any small chemical compound, or a biological entity, such as a protein, sugar, nucleic acid or lipid. Alternatively, modulators can be genetically altered versions of a TAS2R gene. Typically, test compounds will be small chemical molecules and peptides. Essentially any chemical compound can be used as a potential modulator or ligand in the assays and methods disclosed herein, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). There are many suppliers of chemical compounds, including Sigma-Aldrich (St. Louis, Mo.), Fluka Chemika-Biochemica Analytika (Buchs, Switzerland) and the like.

Methods to identify compounds that bind and/or modulate fTAS2R receptors are disclosed. A "TAS2R binding partner" is a compound that directly or indirectly binds a TAS2R polypeptide disclosed herein. In an embodiment, the method comprises contacting TAS2R receptor with a test compound suspected of binding TAS2R receptor; and detecting binding between the compound and the TAS2R receptor. In one variation, a composition comprising a cell expressing TAS2R receptor on its surface is used in the method. In another variation, isolated TAS2R receptor or cell membranes comprising TAS2R receptor are employed. The binding may be measured directly, e. g., by using a labeled compound, or may be measured indirectly. Compounds identified as binding a TAS2R receptor may be further tested in other assays including TAS2R activity assays and/or in vivo models, in order to confirm or quantitate their activity.

"Substantially the same" biological activity refers to a polypeptide fragment, derivative, homolog, analog, or variant retaining at least about 50%, 55%, 60%, 65%, 70%, preferably at least about 75%, 80%, 85%, 90%, more preferably at least about 91%, 92%, 93%, 94%, 95%, and most preferably at least about 96%, 97%, 98%, 99% or greater biological activity of the parent polypeptide. The extent to which a polypeptide fragment, derivative, homolog, analog, or variant retains the biological activity of the parent polypeptide may be assessed by any means available in the art, including, but not limited to, the assays listed or described herein.

Specific binding molecules, including natural ligands and synthetic compounds, can be identified or developed using isolated or recombinant TAS2R products, TAS2R variants, or cells expressing such products. Binding partners are useful for purifying TAS2R products and detection or quantification of TAS2R products in fluid and tissue samples using known immunological procedures. Binding molecules are also useful in modulating (i.e., blocking, inhibiting or stimulating) biological activities of TAS2R, especially those activities involved in signal transduction. Binding molecules also are useful in methods for predicting the taste perception of an organism such as a mammal by detecting a TAS2R polypeptide in a biological sample of a feline.

The term "taste perception" as used herein refers to a response (e.g., biochemical, behavioral) or sensitivity of a TAS2R receptor to a taste stimulus. Modification of taste perception includes an alteration of (enhancement of, reduction of, or change to) a biochemical response, an ingestive response, a taste preference, or a general behavior of a mammal in response to a compound. "Taste perception" does not require, though it can include, transmission of a neural signal resulting in the in vivo sensation of taste by a mammal.

The nucleic acid and amino acid sequence information disclosed herein also makes possible identification of binding partner compounds with which a TAS2R polypeptide or polynucleotide will interact. Methods to identify binding partner compounds include solution assays, in vitro assays wherein TAS2R polypeptides are immobilized, and cell-based assays.

Methods for identifying TAS2R-binding partners are disclosed herein. In solution assays, the methods can comprise the steps of (a) contacting a TAS2R receptor with one or more candidate binding partner compounds and (b) identifying the compounds that bind to the TAS2R receptor. Identification of the compounds that bind the TAS2R receptor can be achieved by isolating the TAS2R polypeptide/binding partner complex, and separating the binding partner compound from the TAS2R polypeptide. In one aspect, the TAS2R polypeptide/binding partner complex is isolated using an antibody immunospecific for either the TAS2R receptor or the candidate binding partner compound.

In still other embodiments, either the TAS2R receptor or the candidate binding partner compound comprises a label or tag that facilitates its isolation, and methods to identify binding partner compounds include a step of isolating the TAS2R polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG tag (Eastman Kodak, Rochester, N.Y.), are well known and routinely used in the art.

In one variation of an in vitro assay, the method comprises the steps of (a) contacting an immobilized TAS2R receptor with a candidate binding partner compound and (b) detecting binding of the candidate compound to the TAS2R receptor. In an alternative embodiment, the candidate binding partner compound is immobilized and binding of TAS2R receptor is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into a feline-specific electronic tongue or biosensor.

Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

In another embodiment, cell-based assays are used to identify binding partner compounds of a TAS2R receptor. In one embodiment, the method comprises the steps of contacting a TAS2R receptor expressed on the surface of a cell with a candidate binding partner compound and detecting binding of the candidate binding partner compound to the TAS2R receptor. In some embodiments, the detection comprises detecting physiological event in the cell caused by the binding of the molecule.

Methods of identifying compounds that bind to either TAS2R receptor or nucleic acid molecules encoding TAS2R receptor are also disclosed. In an embodiment, the method comprises contacting TAS2R receptor, or a nucleic acid molecule encoding the same, with a compound, and determining whether the compound binds TAS2R receptor or a nucleic acid molecule encoding the same. Binding can be determined by any binding assay known to the skilled artisan, including gel-shift assays, Western blots, radiolabeled competition assay, phage-based expression cloning, co-fractionation by chromatography, co-precipitation, cross-linking, interaction trap/two-hybrid analysis, southwestern analysis, and ELISA.

The methods may also use ligands that are attached to a label, such as a radiolabel (e.g., $^{125}I$, $^{35}S$, $^{32}P$, $^{33}P$, $^{3}H$), a fluorescence label, a chemiluminescent label, an enzymic label, and an immunogenic label.

Modulators can include non-peptide molecules such as non-peptide mimetics, non-peptide allosteric effectors, and peptides.

The TAS2R polypeptide or polynucleotide employed in such a test may either be free in solution, attached to a solid support, borne on a cell surface, located intracellularly, or associated with a portion of a cell. One skilled in the art can, for example, measure the formation of complexes between TAS2R receptor or polynucleotide and the compound being tested. Alternatively, one skilled in the art can examine the diminution in complex formation between TAS2R receptor or polynucleotide and its substrate caused by the compound being tested. In some embodiments, the recognition sites of the TAS2R receptor or polynucleotide are coupled with a monitoring system, either electrical or optical. An appropriate chemical stimulus can bind to the receptor's ligand binding domain, changing the receptor conformation to a degree that the coupled electronics or optical changes can be observed on a read-out. In an embodiment, the solid support is formulated into a feline-specific electronic tongue or biosensor.

The term "solid support" refers to a material or group of materials having a rigid or semi-rigid surface or surfaces. Examples of materials include plastics (e.g., polycarbonate), complex carbohydrates (e.g., agarose and sepharose), acrylic resins (e.g., polyacrylamide and latex beads), nitrocellulose, glass, silicon wafers, and positively charged nylon. In some aspects, at least one surface of the solid support can be substantially flat, although in some aspects it may be desirable to physically separate regions for different molecules with, for example, wells, raised regions, pins, etched trenches, or the like. In certain aspects, the solid support(s) will take the form of beads, resins, gels, microspheres, or other geometric configurations.

In another embodiment, high throughput screening (HTS) for compounds having suitable binding affinity to TAS2R receptor is employed. Briefly, large numbers of different small peptide test compounds are synthesized on a solid substrate. The peptide test compounds are contacted with TAS2R receptor and washed. Bound TAS2R receptor is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed TAS2R receptor can be used for HTS binding assays in conjunction with a ligand, such as an amino acid or carbohydrate. The identified peptide is labeled with a suitable radioisotope, including, $^{121}I$, $^{3}H$, $^{35}S$ or $^{32}P$, by methods that are well known to those skilled in the art. Alternatively, the peptides may be labeled by well-known methods with a suitable fluorescent derivative (Baindur et al., Drug Dev. Res., 1994, 33, 373-398; Rogers, Drug Discovery Today, 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand. Alternative methods include a scintillation proximity assay (SPA) or a FlashPlate format in which such separation is unnecessary. Binding of fluorescent ligands can be detected in various ways, including fluorescence energy transfer (FRET), direct spectrophotofluorometric analysis of bound ligand, or fluorescence polarization.

Other assays may be used to identify specific ligands of a TAS2R receptor, including assays that identify ligands of the target protein through measuring direct binding of test ligands to the target, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system, a genetic assay for detecting interactions between two proteins or polypeptides.

Also disclosed are methods of identifying compounds that modulate (i. e., increase or decrease) activity of TAS2R receptor comprising contacting TAS2R receptor with a compound, and determining whether the compound modifies activity of TAS2R receptor. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist.

Agents that modulate (i.e., increase, decrease, or block) TAS2R receptor activity or expression also may be identified, for example, by incubating a putative modulator with a cell containing a TAS2R polypeptide or polynucleotide and determining the effect of the putative modulator on TAS2R receptor activity or expression. The selectivity of a compound that modulates the activity of TAS2R receptor can be evaluated by comparing its effects on TAS2R receptor to its effect on other TAS2R receptors. Selective modulators may include, for example, antibodies and other proteins, peptides, or organic molecules that specifically bind to a TAS2R polypeptide or a TAS2R receptor-encoding nucleic acid. Compounds identified as modulating TAS2R receptor activity may be further tested in other assays including in vivo models, in order to confirm or quantitate their activity.

TAS2R polynucleotides and polypeptides, and their homologs, are useful tools for identifying taste receptor expressing cells, and for examining taste transduction. TAS2R family member-specific reagents that specifically hybridize to TAS2R nucleic acids, such as TAS2R probes and primers, and TAS2R specific reagents that specifically bind to a TAS2R protein, e.g., TAS2R antibodies are used to examine taste cell expression and taste transduction regulation. For example, a TAS2R antibody can be used to identify and/or isolate feline taste cells expressing the particular TAS2R from a mixed feline cell population. For example, polynucleotide probes disclosed herein may be used in tissue distribution studies and diagnostic assays.

Nucleic acid assays for the presence of DNA and RNA for a TAS2R family member in a sample include numerous techniques known to those skilled in the art, such as Southern analysis, Northern analysis, dot blots, RNase protection, S1 analysis, amplification techniques such as polymerase chain reaction (PCR) and ligase chain reaction (LCR), and in situ hybridization. In addition, a TAS2R protein can be detected with the various immunoassay techniques known in the art. The test sample is typically compared to both a positive control (e.g., a sample expressing a recombinant TAS2R protein) and a negative control.

Also provided are kits for screening for modulators of TAS2R family members. Such kits can be prepared from readily available materials and reagents. For example, such kits can comprise any one or more of the following materials: TAS2R nucleic acids or proteins, reaction tubes, and instructions for testing TAS2R activity. Optionally, the kit contains a biologically active TAS2R receptor. A wide variety of kits and components can be prepared, depending upon the intended user of the kit and the particular needs of the user.

Other embodiments of the present invention are described in the following non-limiting Examples.

EXAMPLES

Example 1

Determining Feline Bitter Taste Receptor (TAS2R) Gene and Polypeptide Sequences

In this example, feline TAS2R genes were identified, by querying the NCBI Felis catus whole genome shotgun contigs database with human bitter receptor gene sequences. Human gene sequences used are identified by NCBI Gene IDs in Table 2.

TABLE 2

NCBI Gene IDs for all functional and pseudogene hTAS2Rs used to identify feline bitter genes.

| Human Bitter Receptor gene | Gene ID |
|---|---|
| Functional Genes | |
| TAS2R1 (TAS2R1; TRB7) | 50834 |
| TAS2R3 (TAS2R3) | 50831 |
| TAS2R4 (TAS2R4) | 50832 |
| TAS2R5 (TAS2R5) | 54429 |
| TAS2R7 (TAS2R7; TRB4) | 50837 |
| TAS2R8 (TAS2R8; TRB5) | 50836 |
| TAS2R9 (TAS2R9; TRB6) | 50835 |
| TAS2R10 (TRB2; TAS2R10) | 50839 |
| TAS2R13 (TRB3; TAS2R13) | 50838 |
| TAS2R14 (TRB1; TAS2R14) | 50840 |
| TAS2R16 (TAS2R16) | 50833 |

TABLE 2-continued

NCBI Gene IDs for all functional and pseudogene
hTAS2Rs used to identify feline bitter genes.

| Human Bitter Receptor gene | Gene ID |
|---|---|
| TAS2R19 (TAS2R19; TAS2R23; TAS2R48; MSTP058; TAS2R23; TAS2R48) | 259294 |
| TAS2R20 (TAS2R20; TAS2R49; TAS2R56; TAS2R49) | 259295 |
| TAS2R30 (TAS2R30; TAS2R47; TAS2R47) | 259293 |
| TAS2R31 (TAS2R31; TAS2R44; TAS2R53; TAS2R44) | 259290 |
| TAS2R38 (PTC; TAS2R38; TAS2R61) | 5726 |
| TAS2R39 (TAS2R39; TAS2R57) | 259285 |
| TAS2R40 (GPR60; TAS2R40; TAS2R58) | 259286 |
| TAS2R41 (TAS2R41; TAS2R59) | 259287 |
| TAS2R42 (TAS2R24; TAS2R55; hTAS2R55; TAS2R55) | 353164 |
| TAS2R43 (TAS2R43; TAS2R52) | 259289 |
| TAS2R45 (GPR59; TAS2R45; ZG24P) | 259291 |
| TAS2R46 (TAS2R46; TAS2R54) | 259292 |
| TAS2R50 (TAS2R50; TAS2R51; TAS2R51) | 259296 |
| TAS2R60 (TAS2R56; TAS2R60) | 338398 |
| Pseudogenes | |
| TAS2R2P (PS9; TAS2R2; TAS2R02; TAS2R2) | 338396 |
| TAS2R12P (PS10; TAS2R12; TAS2R12; TAS2R26) | 266656 |
| TAS2R15P (PS8; TAS2R15) | 266657 |
| TAS2R18 (PS4; TAS2R18; TAS2R65; TAS2R65; TAS2R65P) | 338414 |
| TAS2R62P (PS1; TAS2R62; TAS2R62) | 338399 |
| TAS2R63P (PS6; TAS2R63) | 338413 |
| TAS2R64P (PS2; TAS2R64; TAS2R64P) | 338412 |
| TAS2R67P (PS5) | 448991 |
| TAS2R68P (PS7; TAS2R68P) | 100653053 |

Individual contigs among the hits were downloaded for manual identification of start (ATG) and stop (TAA, TGA, or TAG) codons and to determine if the gene is likely full length. When sequences from both feline genome assemblies were obtained, they were compared.

Predicted functional genes were identified based on a set of rules selected to include a protein which is approximately 300 amino acids in length, the start site and stop site are in similar locations as the human protein when the blasted sequences are aligned, then the sequence was compared to the sequence of the orthologous canine bitter gene to verify that similarity was reasonable. Table 3 identifies canine bitter gene sequences used.

TABLE 3

NCBI Gene IDs for all functional
and pseudogene canine TAS2Rs used

| | Canine Bitter Receptor gene | Gene ID |
|---|---|---|
| | Functional Genes | |
| 1 | TAS2R1 (CAFA-TAS2R1) | 100271742 |
| 2 | Cafa-TAS2R2 | 100271741 |
| 3 | TAS2R3 (CAFA-TAS2R3) | 100271736 |
| 4 | TAS2R4 | 100688996 |
| 5 | TAS2R5 (CAFA-TAS2R5) | 100271743 |
| 6 | TAS2R7 (CAFA-TAS2R7) | 100271739 |
| 7 | TAS2R10 (CAFA-TAS2R10) | 100271734 |
| 8 | Cafa-TAS2R12 | 100271738 |
| 9 | TAS2R38 (CAFA-TAS2R38) | 100271737 |
| 10 | TAS2R39 (CAFA-TAS2R39) | 100271735 |
| 11 | TAS2R40 | 608842 |
| 12 | TAS2R41 | 482734 |
| 13 | TAS2R42 (CAFA-TAS2R55) | 100271731 |
| 14 | Cafa-TAS2R43 | 100271744 |
| 15 | TAS2R62-like | 608741 |
| 16 | Cafa-TAS2R67 | 100271740 |
| | Pseudogenes | |
| 1 | TAS2R8P | 100682910 |
| 2 | TAS2R9P | 100686911 |
| 3 | Cafa-TAS2R44P | GenBank: AB249699.1 |
| 4 | TAS2R46-like | 100682759 |
| 5 | TAS2R60-like | 100856773 |
| 6 | TAS2R104-like | 100682833 |

Table 4 below summarizes the full length feline genes identified. The % protein similarity between the feline gene and closest human homologue is presented in the table.

TABLE 4

Full length Feline Bitter Receptor Genes Identified

| Predicted Feline Gene | Functional human homologue | Best % similarity to human sequence |
|---|---|---|
| TAS2R1 | yes | 60.5% |
| TAS2R2 | NO | 74.8% |
| TAS2R3 | yes | 74.4% |
| TAS2R4 | yes | 71.9% |
| TAS2R7 | yes | 74.4% |
| TAS2R9 | yes | 68.3% |
| TAS2R10 | yes | 67.8% |
| TAS2R12 | NO | 51.0% |
| TAS2R38 | yes | 67.6% |
| TAS2R42 | NO | 56.1% |
| TAS2R43 | yes | 59.0% |
| TAS2R44 | yes | 59.9% |
| TAS2R67 | NO | 47.6% |

Cloning of each of the feline bitter genes to confirm the DNA sequence was performed after amplifying the desired gene by polymerase chain reaction (PCR) using the genomic DNA of a single cat. Potential primers to amplify each feline gene were designed using commercial software. Sets of primers were selected from among those designed based on predicted annealing temperature, fidelity, potential for dimerization and mispriming, and location of the desired sequence in order to amplify the feline gene sequence and determine the DNA sequence from isolated feline genomic DNA.

The process of amplification and cloning of a representative gene, TAS2R38, is briefly described. The fTAS2R38 sequence was amplified via PCR using Easy A High Fidelity PCR Cloning Enzyme (Agilent, Santa Clara Calif.), custom primers, and feline genomic DNA as a template.

The resulting PCR product was ligated into the pGEM-T Easy Vector (Promega, Madison Wis.). DH5-α bacterial cells (Life Technologies; Carlsbad, Calif.) were transformed with the vector. Plasmids were purified from cultures of the transformed DH5-alpha cells using the Plasmid Miniprep Kit (Omega BioTec, Norcross, Ga.). Sequencing of the gene using the purified plasmid DNA was performed by the Core DNA Sequencing Facility at the University of Illinois, Champaign-Urbana. The sequencing data was analyzed with Seq- Man Pro (DNAStar, Madison Wis.) to determine the quality of the data and to edit the data.

The gene sequence determined from the isolated feline genomic DNA sequencing was compared against the sequences obtained from the whole genome shotgun contigs and analyzed to identify specific nucleotide differences, predicted protein sequence, and protein structure. Sequences disclosed in the sequence listing for each of the feline bitter taste receptor gene cDNAs and polypeptides are identified by the SEQ ID NOs shown in Table 5.

TABLE 5

SEQ ID NOs of feline bitter taste receptor gene cDNA and polypeptide sequences

| SEQ ID NO. | Feline TAS2R Sequence |
|---|---|
| 1 | R1 cDNA |
| 2 | R1 polypeptide |
| 3 | R2 cDNA |
| 4 | R2 polypeptide |
| 5 | R3 cDNA |
| 6 | R3 polypeptide |
| 7 | R4 cDNA |
| 8 | R4 polypeptide |
| 9 | R7 cDNA |
| 10 | R7 polypeptide |
| 11 | R9 cDNA |
| 12 | R9 polypeptide |
| 13 | R10 cDNA |
| 14 | R10 polypeptide |
| 15 | R12 cDNA |
| 16 | R12 polypeptide |
| 17 | R38 cDNA |
| 18 | R38 polypeptide |
| 19 | R42 cDNA |
| 20 | R42 polypeptide |
| 21 | R43 cDNA |
| 22 | R43 polypeptide |
| 23 | R44 cDNA |
| 24 | R44 polypeptide |
| 25 | R67 cDNA |
| 26 | R67 polypeptide |

In general, the feline gene is named after its homologous human counterpart, as shown in Table 6. However for a feline gene similar to many human genes, such as fTAS2R43, the feline gene is named as its homologous canine counterpart.

TABLE 6

Corresponding genes in felines, canines and humans

| Predicted Feline Gene | Predicted Canine Gene | Human Gene |
|---|---|---|
| TAS2R1 | TAS2R1 | TAS1R1 |
| TAS2R2 | CAFA-T2R2 | TAS2R2P |
| TAS2R3 | TAS2R3 | TAS2R3 |
| TAS2R4 | TAS2R4 | TAS2R4 |
| TAS2R5P | TAS2R5 | TAS2R5 |
| TAS2R7 | TAS2R7 | TAS2R7 |
| TAS2R8P | TAS2R8P | TAS2R8 |
| TAS2R9 | TAS2R9P | TAS2R9 |
| TAS2R10 | TAS2R10 | TAS2R10 |
| TAS2R12 | TAS2R12 | TAS2R12P |
| TAS2R16P | N/A | TAS2R16 |
| TAS2R38 | TAS2R38 | TAS2R38 |
| TAS2R39P | TAS2R39 | TAS2R39 |
| TAS2R40P | TAS2R40 | TAS2R40 |
| TAS2R41P | TAS2R41 | TAS2R41 |
| TAS2R42 | TAS2R42 | hTAS2R42, 18P, 67P |
| TAS2R43 | TAS2R43 | hTAS2R13, 14, 19, 20, 30, 31,43, 45, 46, 50, 15P, 63P, 64P, 68P |
| TAS2R44 | CAFA-T2R44P | hTAS2R13, 14, 19, 20, 30, 31, 43, 45, 46, 50, 15P, 63P, 64P, 68P |
| TAS2R67 | CAFA-T2R67 | hTAS2R42, 18P, 67P |
| TAS2R60P | Tas2R60P-like | TAS2R60 |
| TAS2R62P | TAS2R62-like | TAS2R62P |

A sequence alignment of the 3rd through the 7th transmembrane (TM) regions of several human and feline bitter receptors is shown in FIG. 1. The sequence alignment illustrates the substantial degree of homology of this region in bitter taste receptors of the two species.

A sequence alignment of human TAS2R38 polypeptide (SEQ ID NO.: 31) and feline TAS2R38 polypeptide (SEQ ID NO.: 18) determined from sequencing genomic DNA of five individual cats is shown in FIG. 2. Amino acids in hTAS2R38 that differ from those in fTAS2R38 are boxed in FIG. 2. The positions of the human polymorphisms known to affect taste perception of 6-n-propylthiouracil (PROP), A49P, V262A, I293V (where AVI is a non-taster and PAV is a taster) are shaded grey in FIG. 2. The residues known to be important for phenylthiocarbamide (PTC) binding to the human TAS2R38 receptor are denoted in FIG. 2 by a thick black box (residues 99-100, 103, 255, and 259) These amino acids either directly bind PTC, contribute to the binding pocket, or are involved in receptor activation by associating with other amino acids.

TOPCONS was used to identify the seven transmembrane regions and the extracellular and cytoplasmic loops of each fTAS2R polypeptide. Results of this analysis are presented in Table 1.

Example 2

Expression Systems for Feline TAS2R

A. Generation of Expression Vectors for Feline TAS2R

This example describes generation of an expression vector for a representative feline bitter receptor, TAS2R38.

The full length gene of feline TAS2R38 was amplified by polymerase chain reaction (PCR) using gene-specific primers that span the entire coding region.

The TAS2R38 cDNA was subcloned into an expression cassette based on the plasmid/expression vector pcDNA3.1D-V5His (Life Technologies, Carlsbad, Calif., US), which contains within its multiple cloning sites the nucleotide sequence coding for the FLAG epitope to allow surface detection of the receptor, then the first 45 amino acids of the rat somatostatin receptor subtype 3 (RSS tag) to facilitate cell surface targeting of the transgene, and the nucleotide sequence coding for the herpes simplex virus (HSV) glycoprotein D epitope (HSV epitope) for facilitating immunocytochemical detection (HSV Tag) on the carboxy terminus.

The nucleic acid sequences encoding FLAG, the RSS tag, TAS2R38, and the HSV tag are fused, in that order, in frame to create a construct to allow translation into the receptor protein. The resulting receptor cDNA in the expression vector encodes the joined amino acid sequences of TAS2R38 preceded by the RSS tag and followed by the HSV tag.

The expression vector including the construct is called pcDNA3.11D-FLAGV5His-TAS2R38 and allows for expression of the TAS2R38 protein (SEQ ID NO:18).

Generation of an expression vector for the other fTAS2Rs disclosed herein is analogous. The restriction enzymes used are adapted accordingly.

B. Generation of Cell Lines Transiently Expressing fTAS2R

Cell lines that transiently express a desired TAS2R disclosed herein are generated by transfecting the appropriate expression vector, e.g., pcDNA3.1 D-FLAGV5His-TAS2R38, constructed as described above in Ex. 2A into cells of a eukaryotic cell line (e.g., ATCC #CRL-11268 or Life Technologies, Cat #R700-07).

On day 0, 60,000 cells per well are plated on poly lysine coated, black 96 well plates with clear bottoms (Costar). The following day the cells are transfected with 150 ng TAS2R38 expression vector, e.g., pcDNA3.1D-FLAGV5His (Invitrogen) along with 45 ng of Gα16 chimera containing the last 44 amino acids of rat gustducin (Gα16gust44) with 0.5 ul Lipofectamine 2000 (Invitrogen) per well. Cells are then incubated 22-44 hours at 37° C. 5% $CO_2$.

The expression of fTAS2R38 is evaluated by testing for the presence of a functional response to a known hTAS2R38 ligand (e.g., PTC), determined via automated calcium imaging using a Fluo-4AM (Life Technologies Corporation) Calcium Assay. Fluo-4AM is a fluorescent indicator of intracellular calcium dynamics (change in concentration) and allows monitoring changes in the calcium concentration, particularly an increase in response to receptor activation occurring after agonist exposure.

Generation of cell lines transiently expressing the other fTAS2Rs disclosed herein is analogous.

Expression of the fTAS2Rs in the various cell lines generated is evaluated by flow cytometry. The extracellular FLAG tag was detected with a FLAG-specific antibody conjugated to fluorescein isothiocyanate (FITC). The percentage of cells expressing a given fTAS2R is determined by percent of cells positive for the FITC signal. The level of fTAS2R expression is determined by the geometric mean of the fluorescence intensity measured. The results for each of the expressed fTAS2R are shown in Table 7.

TABLE 7

Flow cytometry results for cell lines transiently expressing fTAS2Rs

| fTAS2R | % of cells expressing fTAS2R | Relative fTAS2R Expression level (Geometric Mean of fluorescence intensity) |
|---|---|---|
| Untransfected cells | 0 | 8,929 |
| TAS2R1 | 38 | 231,625 |
| TAS2R2 | 37 | 295,625 |
| TAS2R3 | 24 | 201,000 |
| TAS2R4 | 36 | 331,125 |
| TAS2R7 | 27 | 144,375 |
| TAS2R9 | 24 | 113,250 |
| TAS2R10 | 30 | 298,500 |
| TAS2R12 | 32 | 258,625 |
| TAS2R38 | 31 | 268,750 |
| TAS2R42 | 25 | 133,375 |
| TAS2R43 | 24 | 246,375 |
| TAS2R44 | 9 | 125,750 |
| TAS2R67 | 12 | 118,000 |

Testing for a functional response of fTAS2R38 to the known hTAS2R38 ligands, PTC and PROP, and of fTAS2R43 to the known hTAS2R43 ligands, aloin, denatonium and saccharine), was determined via automated calcium imaging using the Fluo-4AM (Life Technologies Corporation) Calcium Assay.

The fTAS2R38 was activated 81% over baseline by 100 μM PTC, but was not stimulated by 30 μM PROP. The fTAS2R43 was activated 45% over baseline by 300 μM aloin, and 17% over baseline by 1 mM denatonium, but was not stimulated by 6.7 mM saccharin. Furthermore, the responses to PTC, denatonium and aloin were inhibited by 1 mM probenecid.

Testing for a functional response of each of the other fTAS2Rs disclosed herein is performed by analogous methods using known ligands to a corresponding homolog of each fTAS2R.

C. Generation of Cell Lines Stably Expressing fTAS2R

Cell lines stably expressing fTAS2R are also obtained.

For these experiments, the fTAS2R38 cDNA is subcloned into an expression cassette based on the plasmid/expression vector pcDNA3.1Zeo (Life Technologies, Carlsbad, Calif., US), which contains within its multiple cloning sites the nucleotide sequence coding for the first 45 amino acids of the rat somatostatin receptor subtype 3 (RSS tag) to facilitate cell surface targeting of the transgene, and the nucleotide sequence coding for the herpes simplex virus (HSV) glycoprotein D epitope (HSV epitope) for facilitating immunocytochemical detection (HSV Tag).

The nucleic acid sequences encoding the RSS tag, TAS2R38, and the HSV tag are fused, in that order, in frame to create a construct to allow translation into the receptor protein. The resulting receptor cDNA in the expression vector encodes the joined amino acid sequences of TAS2R38 preceded by the RSS tag and followed by the HSV tag.

In a variation, the nucleic acid sequences encoding the RSS tag, HSV tag, and fTAS2R38 are fused, in that order, in frame to create a construct to allow translation into the receptor protein. The resulting receptor cDNA in the expression vector encodes the joined amino acid sequences of fTAS2R38 preceded by the RSS tag and the HSV tag.

The expression vector including the construct encoding the RSS tag, HSV tag, and fTAS2R38 in that order is called pcDNA3.1Zeo-TAS2R38 and allows for expression of the fTAS2R38 protein (SEQ ID:18).

Generation of an expression vector for the other fTAS2Rs disclosed herein is analogous. The restriction enzymes used are adapted accordingly.

Cell lines that stably express a desired fTAS2R disclosed herein are generated by transfecting the appropriate expression vector, e.g., pcDNA3.1Zeo-TAS2R38, constructed as described above into a eukaryotic host cell line (Life Technologies Cat #R700-07) transformed with the Gα16 chimera containing the last 44 amino acids of rat gustducin, Gα16-gustducin 44 cells, formed as described in WO2004/055048.

On day 0, the Gα16-gustducin 44 cells are plated in a 6-well plate at a density of 900,000 cells per well and grown overnight in a selective growth media (DMEM with 10% (v/v) heat-inactivated fetal bovine serum, 2 mM L-glutamine, 100 units/ml penicillin, 100 μg/ml streptomycin).

On day 1, the medium is exchanged with 2 ml of antibiotic-free and serum-free growth medium. 10 μl Lipofectamine 2000 (Life Technologies Corporation) is dissolved in 250 μl DMEM and incubated for 5 minutes at room temperature. In parallel, 4 μg pcDNA3.1Zeo-TAS2R38 DNA is dissolved in 250 μl DMEM. These two resulting solutions are mixed and incubated for 20 minutes at room temperature before they are added to the cells into the cell culture medium. After 4 hours, the medium is replaced with antibiotic-free, serum-containing growth medium. The cells are incubated in humidified atmosphere (37 C., 5% CO2).

After 24 hours, the cells are re-plated in selective growth medium (DMEM with 10% (v/v) heat-inactivated fetal bovine serum, 2 mM L-glutamine, 100 units/ml penicillin, 100 μg/ml streptomycin, 200 μg/ml G418 and 200 μg/ml zeocin) and are further incubated in a humidified atmosphere (37 C., 5% CO2).

After 2 to 4 weeks of culture (replacing medium as necessary), zeocin-resistant colonies are selected and expanded.

The expression of fTAS2R38 is evaluated by testing for the presence of a functional response to a known hTAS2R38 ligand (e.g., PTC and PROP), determined via automated calcium imaging using the Fluo-4AM (Life Technologies Corporation) Calcium Assay. Fluo-4AM is a fluorescent indicator of intracellular calcium dynamics (change in concentration) and allows monitoring changes in the calcium concentration, particularly an increase in response to receptor activation occurring after agonist exposure. One clone is selected resulting in the Gα16-gustducin 44/TAS2R38 cell line. The Gα16-gustducin 44/TAS2R38 cell line was activated 90% over baseline in the presence of 100 µM PTC but was not activated with 30 µm PROP.

Generation of cell lines stably expressing the other fTAS2Rs disclosed herein is analogous

Example 3

Cell-Based Screening for Ligands and Effectors of Feline TAS2Rs

Identification of agonists, antagonists and modulators of feline TAS2R38 receptor is performed by a cell-based screening assay in which the effect of a test compound on cells transfected with feline TAS2R38 and Gα16gust44 is compared against the effect of the test compound on untransfected cells.

Prior to the screening assay, the cells are loaded with the calcium sensitive dye Fluo-AM (Life Technologies) for one hour at 37° C. as described in Example 2B. The dye is washed out and the cells are assayed in Hank's Balanced Salt Solution (HBSS; Life Technologies) containing 20 mM HEPES in a Flexstation II (Molecular Devices). A 10 fold dilution series 0.01 mM-1 mM of test compounds is used to stimulate the cells. PTC, a known human TAS2R38 agonist, is among the test compounds The stimuli are injected and monitored for 100-180 seconds. Data are analyzed and graphed as a percentage over the baseline signal, which is the reading prior to stimulation.

Stimulation of the fTAS2R38 expressing cell line by a particular test compound is considered to occur when the signal is greater than both the signal from the buffer alone in the receptor expressing cell line and the signal from the untransfected cell line sample injected with the test compound.

Cell based screening for agonists, antagonists, and modulators for the other fTAS2Rs disclosed herein is analogous.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The modifier "about" used in connection with a quantity is inclusive of the stated value and has the meaning dictated by the context (e.g., includes the degree of error associated with measurement of the particular quantity).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Unless defined otherwise, technical and scientific terms used herein have the same meaning as is commonly understood by one of skill in the art to which this invention belongs.

All references are incorporated by reference herein.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising
the amino acid sequence of SEQ ID NO:2, or
an amino acid sequence having at least 95% homology to the sequence of SEQ ID NO:2;
wherein the polypeptide is covalently bound to a label, a solid support, or a lipid monolayer.

2. The polypeptide of claim 1 comprising the amino acid sequence of SEQ ID NO:2.

3. The polypeptide of claim 1 comprising an amino acid sequence having at least 95% homology to SEQ ID NO:2.

4. The polypeptide of claim 1, wherein the polypeptide is covalently bound to a lipid monolayer.

5. The polypeptide of claim 1, wherein the polypeptide is covalently bound to a label.

6. The polypeptide of claim 5, wherein the label is a heterologous polypeptide sequence.

7. The polypeptide of claim 6, wherein the heterologous polypeptide sequence is a membrane targeting sequence or a peptide tag sequence.

8. The polypeptide of claim 5, wherein the label is a radiolabel, a fluorescence label, a chemiluminescent label, an enzymic label, or an immunogenic label.

9. The polypeptide of claim 1, wherein the polypeptide is covalently bound to a solid support.

10. A method for identifying a compound that interacts with a feline TAS2R receptor comprising:
contacting the polypeptide of claim 1 with a test compound, and
detecting interaction between the polypeptide and the test compound.

11. The method of claim 10, wherein the polypeptide is bound to a solid support or expressed in a host cell.

12. A method for identifying a compound which modulates a feline TAS2R receptor which comprises:

contacting a polypeptide of claim 1 with a receptor ligand in the presence or absence of a test compound, and determining whether the test compound modulates binding of the ligand to the polypeptide or activation of the polypeptide by the ligand.

13. A chimeric polypeptide comprising at least one extracellular domain of SEQ ID NO:2 covalently linked to a heterologous polypeptide sequence, wherein the extracellular domain comprises amino acids 68-84; 146-179; or 249-257 of SEQ ID NO:2.

14. A chimeric polypeptide comprising at least one intracellular domain of SEQ ID NO:2 covalently linked to a heterologous polypeptide sequence, wherein the intracellular domain comprises 23-46; 106-124; 201-227; or 279-298 of SEQ ID NO:2.

15. A chimeric polypeptide comprising at least one transmembrane domain of SEQ ID NO:2 covalently linked to a heterologous polypeptide sequence, wherein the transmembrane domain comprises amino acids 2-22, 47-67, 85-105, 125-145, 180-200, 228-248, or 258-278 of SEQ ID NO:2.

16. The chimeric polypeptide of claim 15 comprising the transmembrane domains comprising amino acids 85-105 of SEQ ID NO:2, amino acids 228-248 of SEQ ID NO:2, and amino acids 258-278 of SEQ ID NO:2.

17. The chimeric polypeptide of claim 15 comprising the transmembrane domains comprising amino acids 85-105 of SEQ ID NO:2, amino acids 180-200 of SEQ ID NO: 2, amino acids 228-248 of SEQ ID NO:2, and amino acids 258-278 of SEQ ID NO:2.

18. The chimeric polypeptide of claim 15 comprising the transmembrane domains comprising amino acids 85-105 of SEQ ID NO:2, amino acids 125-145 of SEQ ID NO:2, amino acids 180-200 of SEQ ID NO: 2, amino acids 228-248 of SEQ ID NO:2, and amino acids 258-278 of SEQ ID NO:2.

19. The chimeric polypeptide of claim 15 comprising the transmembrane domains comprising amino acids 2-22 of SEQ ID NO:2, amino acids 47-67 of SEQ ID NO:2, amino acids 85-105 of SEQ ID NO:2, amino acids 125-145 of SEQ ID NO:2, amino acids 180-200 of SEQ ID NO: 2, amino acids 228-248 of SEQ ID NO:2, and amino acids 258-278 of SEQ ID NO:2.

20. The chimeric polypeptide of claim 19 further comprising amino acids 68-84 of SEQ ID NO:2.

* * * * *

SEQUENCE LISTING

<160> NUMBER OF SEQ ID NOS: 31

<210> SEQ ID NO 1
<211> LENGTH: 897
<212> TYPE: DNA
<213> ORGANISM: Felis catus

<400> SEQUENCE: 1

```
atgctagact tttacctcat tatccatttt cttcttccag tgatacaatg tctcatcgga      60
gttttagcaa atggcatcat tgtgatcgtg aatggcactg agttgatcaa gcagagaaag     120
atggttccgt tggatctcct tctttcctgc ctggcgattt ccaggatttg tctgcagtca     180
tttatcttct acattaatct ggttattctc tccttgatcg acttccttcc acttgttaag     240
aattttgcgg ttttcatgtt tgtaaatgaa acgggacttt ggctggccac atggctcggc     300
gttttctact gcgccaagat ctcccccatc gctcacccac tcttcttctg gttgaagagg     360
aggatatcca agttggtgcc atggctgatc atcgggtctc tgcttttttgc ctccatccct     420 ttggtttct acagcaagca tacgtgggtt cttttcccaag aagtcttgtt gagacttttc     480
tccccaaatg caacaactca aatcaaagaa acatctgctt tacagattgt ctttcttgct     540
```

```
aggttttcac cgccgttcat tatcttcctc acttctactc tgctcctggt gttttctctg     600
gggagacata cgtggcagat gagaaacaca gcgacgggca ccagggacgg tagcacaggt     660
gtccatgtga gtgcgcttct gtccattctg tccttcttgg tcctctatct ctcccactac     720
atgacagctg ctttgctctc ttctcacatt tttgagctca gaagcttcat gtttctgttc     780
tgtatcttgg tgttcgggtc ctacccttcg ggacactcta ttatcttaat ttcgggaaat     840
cgtaaactga aacaaaatgc aaagaagttc ctcctccatg ggcagtgctg ccagtga       897
```

<210> SEQ ID NO 2
<211> LENGTH: 298
<212> TYPE: PRT
<213> ORGANISM: Felis catus

<400> SEQUENCE: 2

```
Met Leu Asp Phe Tyr Leu Ile Ile His Phe Leu Leu Pro Val Ile Gln
1               5                   10                  15

Cys Leu Ile Gly Val Leu Ala Asn Gly Ile Ile Val Ile Val Asn Gly
            20                  25                  30

Thr Glu Leu Ile Lys Gln Arg Lys Met Val Pro Leu Asp Leu Leu Leu
        35                  40                  45

Ser Cys Leu Ala Ile Ser Arg Ile Cys Leu Gln Ser Phe Ile Phe Tyr
    50                  55                  60

Ile Asn Leu Val Ile Leu Ser Leu Ile Asp Phe Leu Pro Leu Val Lys
65                  70                  75                  80

Asn Phe Ala Val Phe Met Phe Val Asn Glu Thr Gly Leu Trp Leu Ala
                85                  90                  95

Thr Trp Leu Gly Val Phe Tyr Cys Ala Lys Ile Ser Pro Ile Ala His
            100                 105                 110

Pro Leu Phe Phe Trp Leu Lys Arg Arg Ile Ser Lys Leu Val Pro Trp
        115                 120                 125

Leu Ile Ile Gly Ser Leu Leu Phe Ala Ser Ile Pro Leu Val Phe Tyr
    130                 135                 140

Ser Lys His Thr Trp Val Leu Ser Gln Glu Val Leu Leu Arg Leu Phe
145                 150                 155                 160

Ser Pro Asn Ala Thr Thr Gln Ile Lys Glu Thr Ser Ala Leu Gln Ile
                165                 170                 175

Val Phe Leu Ala Arg Phe Ser Pro Pro Phe Ile Phe Leu Thr Ser
            180                 185                 190

Thr Leu Leu Val Phe Ser Leu Gly Arg His Thr Trp Gln Met Arg
        195                 200                 205

Asn Thr Ala Thr Gly Thr Arg Asp Gly Ser Thr Gly Val His Val Ser
    210                 215                 220

Ala Leu Leu Ser Ile Leu Ser Phe Leu Val Leu Tyr Leu Ser His Tyr
225                 230                 235                 240

Met Thr Ala Ala Leu Leu Ser Ser His Ile Phe Glu Leu Arg Ser Phe
                245                 250                 255

Met Phe Leu Phe Cys Ile Leu Val Phe Gly Ser Tyr Pro Ser Gly His
            260                 265                 270

Ser Ile Ile Leu Ile Ser Gly Asn Arg Lys Leu Lys Gln Asn Ala Lys
        275                 280                 285

Lys Phe Leu Leu His Gly Gln Cys Cys Gln
    290                 295
```

<210> SEQ ID NO 3
<211> LENGTH: 915
<212> TYPE: DNA
<213> ORGANISM: Felis catus

<400> SEQUENCE: 3

```
atggcctcct ctttgtcagc gattcctcac cttatcatca tgtcagcaga atttatcaca      60
gggattacag taaatggatt tcttgtaatc atcaacggta agaattgat caaaagcaga     120
aagctaacac caatgcaact cctttgcata tgtataggga tatcgagatt tggtttgttg     180
atggtgttaa tggtacaaag tttttctct gtgttctttc cactctttta tagggtaaaa     240
atttatggtg catcaatgtt gttcttttgg atgttttta gctctgtcag tctttggttt     300
gccacctgcc tttctgtgtt ttactgcctc aagatatcag gcttcactca atcctatttt     360
ctttggctga aattcaggat ctcaaagtta atgccttggc tgcttctggg aagcctgctg     420
gcctccatga gcattgccgc tgtgtctttg gatgtaggtt accctaaaaa catgaacaat     480
aatgatttcc tcaagaatgc cacgctgaag aagactgaac tcaagatagg gccaattaat     540
ggagtgcttc ttgtcaactt ggcattgcta tttccactag ccatatttgt gatgtgtact     600
tttatgttat tcatttctct ctataggcac actcatcgga tgcaaaacag atctcatggt     660
gttagaaatg ccagcacaga agcccatata aatgcattaa aaacagtgat aacattcttt     720
tgcttctttta tttcttattt tgctgccttc atggccaata tgacattcag tattccttac     780
ggaagtcagt gcttctttgt ggtaaaggac ataatggcag catttccctc tggacattca     840
gttataatca tattgaataa ttctaaattc aacaaccat tcaggagact tctctgcctc     900
aaaaagaatc aatga                                                     915
```

<210> SEQ ID NO 4
<211> LENGTH: 304
<212> TYPE: PRT
<213> ORGANISM: Felis catus

<400> SEQUENCE: 4

```
Met Ala Ser Ser Leu Ser Ala Ile Pro His Leu Ile Ile Met Ser Ala
1               5                   10                  15

Glu Phe Ile Thr Gly Ile Thr Val Asn Gly Phe Leu Val Ile Ile Asn
            20                  25                  30

Gly Lys Glu Leu Ile Lys Ser Arg Lys Leu Thr Pro Met Gln Leu Leu
        35                  40                  45

Cys Ile Cys Ile Gly Ile Ser Arg Phe Gly Leu Leu Met Val Leu Met
    50                  55                  60

Val Gln Ser Phe Phe Ser Val Phe Phe Pro Leu Phe Tyr Arg Val Lys
65                  70                  75                  80

Ile Tyr Gly Ala Ser Met Leu Phe Phe Trp Met Phe Ser Ser Val
                85                  90                  95

Ser Leu Trp Phe Ala Thr Cys Leu Ser Val Phe Tyr Cys Leu Lys Ile
            100                 105                 110

Ser Gly Phe Thr Gln Ser Tyr Phe Leu Trp Leu Lys Phe Arg Ile Ser
        115                 120                 125

Lys Leu Met Pro Trp Leu Leu Leu Gly Ser Leu Ala Ser Met Ser
    130                 135                 140

Ile Ala Ala Val Ser Leu Asp Val Gly Tyr Pro Lys Asn Met Asn Asn
145                 150                 155                 160

Asn Asp Phe Leu Lys Asn Ala Thr Leu Lys Lys Thr Glu Leu Lys Ile
                165                 170                 175
```

```
Gly Pro Ile Asn Gly Val Leu Leu Val Asn Leu Ala Leu Leu Phe Pro
                180                 185                 190

Leu Ala Ile Phe Val Met Cys Thr Phe Met Leu Phe Ile Ser Leu Tyr
                195                 200                 205

Arg His Thr His Arg Met Gln Asn Arg Ser His Gly Val Arg Asn Ala
210                 215                 220

Ser Thr Glu Ala His Ile Asn Ala Leu Lys Thr Val Ile Thr Phe Phe
225                 230                 235                 240

Cys Phe Phe Ile Ser Tyr Phe Ala Ala Phe Met Ala Asn Met Thr Phe
                245                 250                 255

Ser Ile Pro Tyr Gly Ser Gln Cys Phe Val Val Lys Asp Ile Met
                260                 265                 270

Ala Ala Phe Pro Ser Gly His Ser Val Ile Ile Leu Asn Asn Ser
                275                 280                 285

Lys Phe Gln Gln Pro Phe Arg Arg Leu Leu Cys Leu Lys Lys Asn Gln
                290                 295                 300
```

<210> SEQ ID NO 5
<211> LENGTH: 951
<212> TYPE: DNA
<213> ORGANISM: Felis catus

<400> SEQUENCE: 5

```
atgtcagggc tccacaagtg ggtgtttctg gttctgtctg ccactcagtt cattctgggg      60
atgctgggga tggtttcat agtgttggtc agtggcagca gttggtttaa gaataagaca      120
atctctttgt ctgacttcat catcgctaac ctggctctct ccaggatcgt tctgctgtgg      180
attctcttgg ttgatggtgt tttaattgtg ttctcttcca agtgcatga tgaagggata      240
ataatgcaaa ttattgatat tttctggaca tttacaaacc acctgagcat ttggcttgcc      300
acctgtctca gtgtcctcta ctgcctgaaa attgccagtt tctctcaccc tacattcctc      360
tggctcaagt ggagagtttc caggatggtc gtacagatga tcttgggtgc gctggtctta      420
tcgtgtgcca gtgccctgtc tctgatccat gaatttaaga tgtattctat tctcggtggg      480
atcgatggca cagggaatgt gactgagcac tttagaaaga aagaaatga atataaattg      540
atccatgttc ttgggactct gtggaacctg cctcctctga ttgtgtctct ggcctcctac      600
tttctgctca tcgtctctct ggggaggcac acgcagcgga tggagcaaag cggcaccagc      660
tccggagatc aagcgctga ggcccacaag agggccatca aaatcatcct ctccttcctc      720
cttctcttcc tgctttactt tcttgccttt ttaattacat catccagtta tttcatacca      780
ggaactgaga tggtgaagat aattggagaa ctcattacca tgttttatcc tgctagccac      840
tcattcattc tcattctggg aaacagcaag ctgaagcata tgtttgtggg gatgctgcgg      900
tgtgagtctg tcatctgaa gcctggatcc aaaggacctg tttccctgta g               951
```

<210> SEQ ID NO 6
<211> LENGTH: 316
<212> TYPE: PRT
<213> ORGANISM: Felis catus

<400> SEQUENCE: 6

```
Met Ser Gly Leu His Lys Trp Val Phe Leu Val Leu Ser Ala Thr Gln
1               5                   10                  15

Phe Ile Leu Gly Met Leu Gly Asn Gly Phe Ile Val Leu Val Ser Gly
                20                  25                  30
```

```
Ser Ser Trp Phe Lys Asn Lys Thr Ile Ser Leu Ser Asp Phe Ile Ile
        35                  40                  45

Ala Asn Leu Ala Leu Ser Arg Ile Val Leu Leu Trp Ile Leu Leu Val
 50                  55                  60

Asp Gly Val Leu Ile Val Phe Ser Ser Lys Val His Asp Glu Gly Ile
 65                  70                  75                  80

Ile Met Gln Ile Ile Asp Ile Phe Trp Thr Phe Thr Asn His Leu Ser
                 85                  90                  95

Ile Trp Leu Ala Thr Cys Leu Ser Val Leu Tyr Cys Leu Lys Ile Ala
                100                 105                 110

Ser Phe Ser His Pro Thr Phe Leu Trp Leu Lys Trp Arg Val Ser Arg
            115                 120                 125

Met Val Val Gln Met Ile Leu Gly Ala Leu Val Leu Ser Cys Ala Ser
        130                 135                 140

Ala Leu Ser Leu Ile His Glu Phe Lys Met Tyr Ser Ile Leu Gly Gly
145                 150                 155                 160

Ile Asp Gly Thr Gly Asn Val Thr Glu His Phe Arg Lys Lys Arg Asn
                165                 170                 175

Glu Tyr Lys Leu Ile His Val Leu Gly Thr Leu Trp Asn Leu Pro Pro
            180                 185                 190

Leu Ile Val Ser Leu Ala Ser Tyr Phe Leu Leu Ile Val Ser Leu Gly
        195                 200                 205

Arg His Thr Gln Arg Met Glu Gln Ser Gly Thr Ser Ser Gly Asp Pro
    210                 215                 220

Ser Ala Glu Ala His Lys Arg Ala Ile Lys Ile Leu Ser Phe Leu
225                 230                 235                 240

Leu Leu Phe Leu Leu Tyr Phe Leu Ala Phe Leu Ile Thr Ser Ser Ser
                245                 250                 255

Tyr Phe Ile Pro Gly Thr Glu Met Val Lys Ile Ile Gly Glu Leu Ile
                260                 265                 270

Thr Met Phe Tyr Pro Ala Ser His Ser Phe Ile Leu Ile Leu Gly Asn
            275                 280                 285

Ser Lys Leu Lys His Met Phe Val Gly Met Leu Arg Cys Glu Ser Gly
    290                 295                 300

His Leu Lys Pro Gly Ser Lys Gly Pro Val Ser Leu
305                 310                 315

<210> SEQ ID NO 7
<211> LENGTH: 921
<212> TYPE: DNA
<213> ORGANISM: Felis catus

<400> SEQUENCE: 7
atgcatcaga tactcttctt atctgctctt actgtctcag caattttgaa ttttgtagga      60
ctcgttgtaa atctgtttat cgtagtggtc aactacagga cttgggtcca aagccacaga    120
atctcctctt ctaataggat cctgttcagc ttgggcgtca ccagatttat tatgctagga    180
ctgtttctcc tgaacattat ctacctgttc acctctccac atgtcgaaag gtcagtccac    240
ctatccactt ttttcctgtt gtgttggatg ttttggagt ctactagtct ctggcttgta     300
accttgctca atgccttgta ctgcgtgaag attactgact ccaacactc agtattcctc     360 ctgctgaaac gaaagctgtc cccaaagatc cccaggctgc tgctggcctg cgtgctgatc    420
tctgccttct ccactctcct gtatgttgtg ctcacacaaa catcaccctt cctgagcttc    480
ctgactggga gcaatggtac agtatgtgac atcaataaga gcatcttgtc tttggtgacc    540
```

```
tccttggtcc tgagctcctt tctccagttc atcatgaatg tgacttccgc ttccttgtta      600
atacattcct tgaggagaca tatacagaag atgcagaaaa acgccactga tttttggaat      660
ccccagactg aagctcatat gggtgctatg aagctaatga tctatttcct catcctctac      720
attccatatt cacttgctac cctgctacag tatctccctt ccgtacggat ggatttggga      780
gccacatcca tctgtatgat tatttccacc ttttatcctc caggacattc tgttctcatt      840
attctcacac atcctaaact gaaaacaaaa gcaagaaga ttctttgttt caacatatgg       900
tggaatttca gtagtaaata g                                                921
```

<210> SEQ ID NO 8
<211> LENGTH: 306
<212> TYPE: PRT
<213> ORGANISM: Felis catus

<400> SEQUENCE: 8

```
Met His Gln Ile Leu Phe Leu Ser Ala Leu Thr Val Ser Ala Ile Leu
1               5                   10                  15

Asn Phe Val Gly Leu Val Val Asn Leu Phe Ile Val Val Asn Tyr
            20                  25                  30

Arg Thr Trp Val Gln Ser His Arg Ile Ser Ser Ser Asn Arg Ile Leu
        35                  40                  45

Phe Ser Leu Gly Val Thr Arg Phe Ile Met Leu Gly Leu Phe Leu Leu
    50                  55                  60

Asn Ile Ile Tyr Leu Phe Thr Ser Pro His Val Glu Arg Ser Val His
65                  70                  75                  80

Leu Ser Thr Phe Phe Leu Leu Cys Trp Met Phe Leu Glu Ser Thr Ser
                85                  90                  95

Leu Trp Leu Val Thr Leu Leu Asn Ala Leu Tyr Cys Val Lys Ile Thr
            100                 105                 110

Asp Phe Gln His Ser Val Phe Leu Leu Lys Arg Lys Leu Ser Pro
        115                 120                 125

Lys Ile Pro Arg Leu Leu Leu Ala Cys Val Leu Ile Ser Ala Phe Ser
    130                 135                 140

Thr Leu Leu Tyr Val Val Leu Thr Gln Thr Ser Pro Phe Pro Glu Leu
145                 150                 155                 160

Leu Thr Gly Ser Asn Gly Thr Val Cys Asp Ile Asn Lys Ser Ile Leu
                165                 170                 175

Ser Leu Val Thr Ser Leu Val Leu Ser Ser Phe Leu Gln Phe Ile Met
            180                 185                 190

Asn Val Thr Ser Ala Ser Leu Leu Ile His Ser Leu Arg Arg His Ile
        195                 200                 205

Gln Lys Met Gln Lys Asn Ala Thr Asp Phe Trp Asn Pro Gln Thr Glu
    210                 215                 220

Ala His Met Gly Ala Met Lys Leu Met Ile Tyr Phe Leu Ile Leu Tyr
225                 230                 235                 240

Ile Pro Tyr Ser Leu Ala Thr Leu Leu Gln Tyr Leu Pro Ser Val Arg
                245                 250                 255

Met Asp Leu Gly Ala Thr Ser Ile Cys Met Ile Ile Ser Thr Phe Tyr
            260                 265                 270

Pro Pro Gly His Ser Val Leu Ile Ile Leu Thr His Pro Lys Leu Lys
        275                 280                 285

Thr Lys Ala Lys Lys Ile Leu Cys Phe Asn Ile Trp Trp Asn Phe Ser
    290                 295                 300
```

Ser Lys
305

<210> SEQ ID NO 9
<211> LENGTH: 936
<212> TYPE: DNA
<213> ORGANISM: Felis catus

<400> SEQUENCE: 9

| | | | | | |
|---|---|---|---|---|---|
| atgctggata | aagtggagag | caccttgatg | ctcatagcag | ctggagaatt | tgcaatgggg | 60 |
| attttaggga | tgcattcat | tggattggta | aactgcatga | ctggatcaa | gaataggaag | 120 |
| attgcctcca | ttgacttaat | cctcacaagt | ctggccatat | ccagaatttg | tctattatgt | 180 |
| atcatactat | tagactattt | tatactgggg | ctgtatccag | atgtctatac | taccggtaaa | 240 |
| aaaatgagaa | tcattgactt | cttctggacg | ctcaccaacc | acctaaatgt | ctggtttgcc | 300 |
| acctgcctca | gcgtcttcta | tttcctcaag | atcgcgaatt | tcttccatcc | ccttttcctc | 360 |
| tggatgaagt | ggaaaattga | cagtgcgatt | cctaggatcc | tgctgggatg | cttggccttc | 420 |
| tctgtgttca | ttagccttgt | tgtctctgag | aatctgaacg | atgatttcag | gtcttgtgtt | 480 |
| aaggtaaaga | agaaaacaaa | cataactgtg | aaatgcagag | taaataaagc | ccaatatgct | 540 |
| tctgtcaaga | tttgcctcaa | cctgttgacg | ctattcccct | tttccgtgtc | cgtgatctca | 600 |
| tttctcctct | tgctcctctc | cctgtggaga | cataccaggc | agatgaagat | cagtgccacg | 660 |
| gggtgcaggg | accccagcat | agaagcccat | gtgggagcca | tgaaagctgt | catctccttc | 720 |
| ctcctccttt | tcattgctta | ctatttggct | tttctcgtag | ccacctccag | ctactttatg | 780 |
| ccagagactg | aactagctgt | gatgattggt | gagttgatag | ctctcatcta | tccaagccat | 840 |
| tcattgattc | taattctggg | gaacaataaa | ttacggcagg | cgtctctaag | ggtgctgtgg | 900 |
| aaagtaaagt | gtatcctaaa | aagaagaaat | cactaa | | | 936 |

<210> SEQ ID NO 10
<211> LENGTH: 311
<212> TYPE: PRT
<213> ORGANISM: Felis catus

<400> SEQUENCE: 10

Met Leu Asp Lys Val Glu Ser Thr Leu Met Leu Ile Ala Ala Gly Glu
1               5                   10                  15

Phe Ala Met Gly Ile Leu Gly Asn Ala Phe Ile Gly Leu Val Asn Cys
            20                  25                  30

Met Asn Trp Ile Lys Asn Arg Lys Ile Ala Ser Ile Asp Leu Ile Leu
        35                  40                  45

Thr Ser Leu Ala Ile Ser Arg Ile Cys Leu Leu Cys Ile Ile Leu Leu
    50                  55                  60

Asp Tyr Phe Ile Leu Gly Leu Tyr Pro Asp Val Tyr Thr Thr Gly Lys
65                  70                  75                  80

Lys Met Arg Ile Ile Asp Phe Phe Trp Thr Leu Thr Asn His Leu Asn
                85                  90                  95

Val Trp Phe Ala Thr Cys Leu Ser Val Phe Tyr Phe Leu Lys Ile Ala
            100                 105                 110

Asn Phe Phe His Pro Leu Phe Leu Trp Met Lys Trp Lys Ile Asp Ser
        115                 120                 125

Ala Ile Pro Arg Ile Leu Leu Gly Cys Leu Ala Phe Ser Val Phe Ile
    130                 135                 140

Ser Leu Val Val Ser Glu Asn Leu Asn Asp Asp Phe Arg Ser Cys Val
145                 150                 155                 160

Lys Val Lys Lys Thr Asn Ile Thr Val Lys Cys Arg Val Asn Lys
            165                 170                 175

Ala Gln Tyr Ala Ser Val Lys Ile Cys Leu Asn Leu Leu Thr Leu Phe
            180                 185                 190

Pro Phe Ser Val Ser Val Ile Ser Phe Leu Leu Leu Leu Ser Leu
            195                 200                 205

Trp Arg His Thr Arg Gln Met Lys Ile Ser Ala Thr Gly Cys Arg Asp
        210                 215                 220

Pro Ser Ile Glu Ala His Val Gly Ala Met Lys Ala Val Ile Ser Phe
225                 230                 235                 240

Leu Leu Leu Phe Ile Ala Tyr Tyr Leu Ala Phe Leu Val Ala Thr Ser
                245                 250                 255

Ser Tyr Phe Met Pro Glu Thr Glu Leu Ala Val Met Ile Gly Glu Leu
            260                 265                 270

Ile Ala Leu Ile Tyr Pro Ser His Ser Leu Ile Leu Leu Gly Asn
            275                 280                 285

Asn Lys Leu Arg Gln Ala Ser Leu Arg Val Leu Trp Lys Val Lys Cys
290                 295                 300

Ile Leu Lys Arg Arg Asn His
305                 310

<210> SEQ ID NO 11
<211> LENGTH: 1014
<212> TYPE: DNA
<213> ORGANISM: Felis catus

<400> SEQUENCE: 11
atgccaagtg cagtggaggt aatatatatg gtcttgattg ctggtgaatt gactatagga      60
atctggggaa atggatttat tgtactggtt aactgcactg gttggctcca aaggcgagat     120
agctccgtga ttgacatcat cctggtgagt ttggccatct ccagaatctg tgtgttgtgt     180
gtggtatctg cagaaggctt tgttctgctg ctctctccac atgcgtatgc tcaaaatgag     240
acaataaaca ccttggatgc tttctggaca ctgagcaacc attcaagtgt ctggttcact     300
gcttgcctca gcatttttcta cttactgaag atagccaaca tatcccaccc ggtgttcctc     360
tggctgaagc taaacgttac cagagtcgtc ctggggcttt ttctggcgtc cttcctcacc     420
tccataatta ttagtgtctt tttgaaagag ggatcctggg gtcacgtcga agtcaatcac     480
gaggaaaaca taacttggga attcagagtg agtaaagccc caagcgcttt caaactgatt     540
atcctgaacc tgggggctct agttcccttt gctctgtgcc taatctcctt tgtcttgtta     600
cttttctccc tctttagaca cgctaagcag atgcaacttt acgccaccgg tccagggac     660 tgtagcacag aggcacacat gagggccata aaggcagtga ccatctttct gcttttcttc     720
atcatgtact atgcagtctt tcttgtagtc acttctagct tcctgattcc tcaaggacgg     780
ttagtgctga tgtttggtgg catagtcact gtcattttcc catcaagcca ttcgttcatc     840
ctgatcatgg caacagcaa gctgagggag cctttctga aggtgctaag gtgtgtgaag     900
ggcttccaca aaagaaggaa acctcttgtt ccgcagagaa tcctgaatac ggggagaaag     960
aaatcaacaa aagactgtct cccttctccc cgggggttac attcatttgc ttaa          1014

<210> SEQ ID NO 12
<211> LENGTH: 337
<212> TYPE: PRT

<213> ORGANISM: Felis catus

<400> SEQUENCE: 12

```
Met Pro Ser Ala Val Glu Val Ile Tyr Met Val Leu Ile Ala Gly Glu
1               5                   10                  15
Leu Thr Ile Gly Ile Trp Gly Asn Gly Phe Ile Val Leu Val Asn Cys
            20                  25                  30
Thr Gly Trp Leu Gln Arg Arg Asp Ser Ser Val Ile Asp Ile Ile Leu
        35                  40                  45
Val Ser Leu Ala Ile Ser Arg Ile Cys Val Leu Cys Val Val Ser Ala
    50                  55                  60
Glu Gly Phe Val Leu Leu Leu Ser Pro His Ala Tyr Ala Gln Asn Glu
65                  70                  75                  80
Thr Ile Asn Thr Leu Asp Ala Phe Trp Thr Leu Ser Asn His Ser Ser
                85                  90                  95
Val Trp Phe Thr Ala Cys Leu Ser Ile Phe Tyr Leu Leu Lys Ile Ala
            100                 105                 110
Asn Ile Ser His Pro Val Phe Leu Trp Leu Lys Leu Asn Val Thr Arg
        115                 120                 125
Val Val Leu Gly Leu Phe Leu Ala Ser Phe Leu Thr Ser Ile Ile Ile
    130                 135                 140
Ser Val Phe Leu Lys Glu Gly Ser Trp Gly His Val Glu Val Asn His
145                 150                 155                 160
Glu Glu Asn Ile Thr Trp Glu Phe Arg Val Ser Lys Ala Pro Ser Ala
                165                 170                 175
Phe Lys Leu Ile Ile Leu Asn Leu Gly Ala Leu Val Pro Phe Ala Leu
            180                 185                 190
Cys Leu Ile Ser Phe Val Leu Leu Leu Phe Ser Leu Phe Arg His Ala
        195                 200                 205
Lys Gln Met Gln Leu Tyr Ala Thr Gly Ser Arg Asp Cys Ser Thr Glu
    210                 215                 220
Ala His Met Arg Ala Ile Lys Ala Val Thr Ile Phe Leu Leu Phe Phe
225                 230                 235                 240
Ile Met Tyr Tyr Ala Val Phe Leu Val Val Thr Ser Ser Phe Leu Ile
                245                 250                 255
Pro Gln Gly Arg Val Val Leu Met Phe Gly Gly Ile Val Thr Val Ile
            260                 265                 270
Phe Pro Ser Ser His Ser Phe Ile Leu Ile Met Gly Asn Ser Lys Leu
        275                 280                 285
Arg Glu Ala Phe Leu Lys Val Leu Arg Cys Val Lys Gly Phe His Lys
    290                 295                 300
Arg Arg Lys Pro Leu Val Pro Gln Arg Ile Leu Asn Thr Gly Arg Lys
305                 310                 315                 320
Lys Ser Thr Lys Asp Cys Leu Pro Ser Pro Arg Gly Leu His Ser Phe
                325                 330                 335
Ala
```

<210> SEQ ID NO 13
<211> LENGTH: 903
<212> TYPE: DNA
<213> ORGANISM: Felis catus

<400> SEQUENCE: 13

```
atgttaagca tagtggaagg ccttctcatt tttatagcag ttagtgaatc agtactgggg    60
```

```
gttttaggga atggatttat tggacttgta aactgtatgg actgtgtgaa gaacaaaaag    120
ttttctatga ttggcttcat cttcaccggc ttagctactt ccagaatttg tctgatattg    180
atagtaatgg cagatggatt tataaagata ttctctccag atatgtactc ttctggtcac    240
ctaattgatt atattagtta cttatggata attatcaatc aatcaaacat ctggtttgcc    300
accagcctca gcaccttcta cttcctgaag atagcaaatt tttcccacca catgtttctc    360
tggttgaagg gtagaatcaa ttgggttctt ccccttctga tgggatcctt gtttatttca    420 tggctctttta cgttccctca aattgtgaag attcttagcg acagtaaagt ggggaatgga    480
aacgcaacct ggcagctcaa catgccgaag agtgagttct taactaagca gattttggtc    540
aacataggag tccttctcct cttcacgcta ttcctgatta catgtttcct gttaatcatt    600 tcccttttgga gacacagcag gcggatgcaa ttgaatgtca ctggattcca agacccagt    660 acagaagcgc atatgaaagc catgaaagtt ttgatatctt tcatcatcct ctttatcttg    720
cattttatag gcctggccat agaaatagca tgcttcacaa tgccagaaaa aaaattgctg    780 tttattttttg gtatgacgac cacagtcttg taccctggg gtcactcatt tatcctcatt    840
ctcggaaaca gcaagctaaa gcaagcctct ctgagagcac tgcagcaggt caagtgctgt    900
taa                                                                  903
```

<210> SEQ ID NO 14
<211> LENGTH: 300
<212> TYPE: PRT
<213> ORGANISM: Felis catus

<400> SEQUENCE: 14

```
Met Leu Ser Ile Val Glu Gly Leu Leu Ile Phe Ile Ala Val Ser Glu
1               5                  10                  15

Ser Val Leu Gly Val Leu Gly Asn Gly Phe Ile Gly Leu Val Asn Cys
            20                  25                  30

Met Asp Cys Val Lys Asn Lys Lys Phe Ser Met Ile Gly Phe Ile Phe
        35                  40                  45

Thr Gly Leu Ala Thr Ser Arg Ile Cys Leu Ile Leu Ile Val Met Ala
    50                  55                  60

Asp Gly Phe Ile Lys Ile Phe Ser Pro Asp Met Tyr Ser Ser Gly His
65                  70                  75                  80

Leu Ile Asp Tyr Ile Ser Tyr Leu Trp Ile Ile Asn Gln Ser Asn
            85                  90                  95

Ile Trp Phe Ala Thr Ser Leu Ser Thr Phe Tyr Phe Leu Lys Ile Ala
            100                 105                 110

Asn Phe Ser His His Met Phe Leu Trp Leu Lys Gly Arg Ile Asn Trp
        115                 120                 125

Val Leu Pro Leu Leu Met Gly Ser Leu Phe Ile Ser Trp Leu Phe Thr
    130                 135                 140

Phe Pro Gln Ile Val Lys Ile Leu Ser Asp Ser Lys Val Gly Asn Gly
145                 150                 155                 160

Asn Ala Thr Trp Gln Leu Asn Met Pro Lys Ser Glu Phe Leu Thr Lys
            165                 170                 175

Gln Ile Leu Val Asn Ile Gly Val Leu Leu Leu Phe Thr Leu Phe Leu
            180                 185                 190

Ile Thr Cys Phe Leu Leu Ile Ile Ser Leu Trp Arg His Ser Arg Arg
        195                 200                 205

Met Gln Leu Asn Val Thr Gly Phe Gln Asp Pro Ser Thr Glu Ala His
    210                 215                 220
```

Met Lys Ala Met Lys Val Leu Ile Ser Phe Ile Ile Leu Phe Ile Leu
225                 230                 235                 240

His Phe Ile Gly Leu Ala Ile Glu Ile Ala Cys Phe Thr Met Pro Glu
            245                 250                 255

Lys Lys Leu Leu Phe Ile Phe Gly Met Thr Thr Thr Val Leu Tyr Pro
        260                 265                 270

Trp Gly His Ser Phe Ile Leu Ile Leu Gly Asn Ser Lys Leu Lys Gln
    275                 280                 285

Ala Ser Leu Arg Ala Leu Gln Gln Val Lys Cys Cys
    290                 295                 300

<210> SEQ ID NO 15
<211> LENGTH: 930
<212> TYPE: DNA
<213> ORGANISM: Felis catus

<400> SEQUENCE: 15
atggcaagcg tattgaagaa tgtatttatg atactgtttg ctggagaatt cataatgggg      60
attttgggaa atggattcat tatattggtt aactgtattg actggatcag gaactggaaa     120
ttcttcgtaa ttgactttat tattacctgc ctagctattt ccagaatagt tctgttgtgc     180
ataataattt taggcatagg tttagatgta ccttgtgaag aaatatggaa caagaataat     240
caactaataa ggtttgaaat cctctggaca ggatccaatt atttctgcat aacctgtacc     300
acctgcctca gtgtcttcta tttcttcaag atagccaact tttccaaccc tcttttcctc     360
tggataaaat ggagaattca caagtgctt ctcacgattg tactggccgc agtcttctct     420
ttctgcttgt ctcttccctt taaggataca gtgttcacga gtctgatcaa aacaaggta      480 aacgcggaaa gaaattggac agtgagtttc acaacgagaa catatgagtt atttttgtct     540
catatgctcc tgaacataat gttcatcatc cctttgcag tgtctctggc ttcctttgtc      600
cttttgatct gttccttatg gagccacacc aggcagatga agggcagagg tggggatcct     660
accacaaaag ttcacgtgag agccatgaag gctatgattt cattcctact cttcttcttt     720
atgtactatt tgagcactat tatgatgaat ttggcctacg tcatcctaga tagtttggtg     780
gcaaagattt ttgctaatac actagtattt ttatatccat ctggccatac atttcttctg     840
attttatgga ccagcaaatt gaaacaggct tctctctgtg tcctgaagaa gctgaagtgc     900
ctgcatctaa ggaaacccac acgcccataa                                      930

<210> SEQ ID NO 16
<211> LENGTH: 309
<212> TYPE: PRT
<213> ORGANISM: Felis catus

<400> SEQUENCE: 16

Met Ala Ser Val Leu Lys Asn Val Phe Met Ile Leu Phe Ala Gly Glu
1               5                   10                  15

Phe Ile Met Gly Ile Leu Gly Asn Gly Phe Ile Ile Leu Val Asn Cys
            20                  25                  30

Ile Asp Trp Ile Arg Asn Trp Lys Phe Phe Val Ile Asp Phe Ile Ile
        35                  40                  45

Thr Cys Leu Ala Ile Ser Arg Ile Val Leu Leu Cys Ile Ile Ile Leu
    50                  55                  60

Gly Ile Gly Leu Asp Val Pro Cys Glu Glu Ile Trp Asn Lys Asn Asn
65                  70                  75                  80

Gln Leu Ile Arg Phe Glu Ile Leu Trp Thr Gly Ser Asn Tyr Phe Cys
                85                  90                  95

Ile Thr Cys Thr Thr Cys Leu Ser Val Phe Tyr Phe Lys Ile Ala
        100                 105                 110

Asn Phe Ser Asn Pro Leu Phe Leu Trp Ile Lys Trp Arg Ile His Lys
            115                 120                 125

Val Leu Leu Thr Ile Val Leu Ala Ala Val Phe Ser Phe Cys Leu Ser
130                 135                 140

Leu Pro Phe Lys Asp Thr Val Phe Thr Ser Leu Ile Lys Asn Lys Val
145                 150                 155                 160

Asn Ala Glu Arg Asn Trp Thr Val Ser Phe Thr Thr Arg Thr Tyr Glu
                165                 170                 175

Leu Phe Leu Ser His Met Leu Leu Asn Ile Met Phe Ile Ile Pro Phe
            180                 185                 190

Ala Val Ser Leu Ala Ser Phe Val Leu Leu Ile Cys Ser Leu Trp Ser
        195                 200                 205

His Thr Arg Gln Met Lys Gly Arg Gly Gly Asp Pro Thr Thr Lys Val
    210                 215                 220

His Val Arg Ala Met Lys Ala Met Ile Ser Phe Leu Leu Phe Phe Phe
225                 230                 235                 240

Met Tyr Tyr Leu Ser Thr Ile Met Met Asn Leu Ala Tyr Val Ile Leu
                245                 250                 255

Asp Ser Leu Val Ala Lys Ile Phe Ala Asn Thr Leu Val Phe Leu Tyr
            260                 265                 270

Pro Ser Gly His Thr Phe Leu Leu Ile Leu Trp Thr Ser Lys Leu Lys
        275                 280                 285

Gln Ala Ser Leu Cys Val Leu Lys Lys Leu Lys Cys Leu His Leu Arg
    290                 295                 300

Lys Pro Thr Arg Pro
305

<210> SEQ ID NO 17
<211> LENGTH: 1005
<212> TYPE: DNA
<213> ORGANISM: Felis catus

<400> SEQUENCE: 17

```
atgttggctc tgactcctgt cataactgtg tcctatgaag tcaagagtgc atttctattc      60
ctttcaatcc tggaatttac agtgggggtc ctggccaatg ccttcatttt cctggtgaat     120
ttttgggacg tggtgaggaa gcagccactg agcaactgtg atcttattct ctgagtctc     180
agcctcaccc ggcttttcct gcacgggctg ctgtttctgg atgccctcca gcttacatac     240
ttccagagga tgaaagatcc gctgagcctc agctaccaga ccatcatcat gctctggatg     300
atcacaaacc aagttgggct gtggctcacc acctgcctca gtcttctcta ctgctccaag     360
attgcccgtt tctctcacac cctcctgcac tgtgtggcaa gctgggtctc cggaaggtc      420
ccccagatgc tcctgggtgc aatgcttttc tcttgtatct gcaccgccat ctgtttgggg     480
gacttttta gtagatctgg cttcacatt acaactatgc tattcgtgaa taatacagaa       540
ttcaatttgc aaattgcaaa actcagtttc tatcactcct tcatcttctg cacactggcg     600
tccatcccgt cgttgttatt ttttctgatt tcttctgggg tgctgattgt ctccctgggg     660
aggcacatga ggacaatgag ggccaaaacc aaagactccc acgacccag cctggaagcc      720
catatcaaag ccctccgatc tcttgtctcc tttctctgcc tctatgtggt gtcattctgt     780
```

```
gctgccctcg tttcagtgcc tttactgatg ctgtggcaca acaagatcgg ggtaatgatc    840
tgtgtgggga tcctagcagc ttgtccctcg atacatgcag caatcctgat ctcaggcaat    900
gccaagctga ggagagctgt ggagaccatt ctactctggg ttcagaacag cctaaagata    960
ggggcagacc acaaggcaga tgccaggact ccaggcctat gttga                  1005
```

<210> SEQ ID NO 18
<211> LENGTH: 334
<212> TYPE: PRT
<213> ORGANISM: Felis catus

<400> SEQUENCE: 18

```
Met Leu Ala Leu Thr Pro Val Ile Thr Val Ser Tyr Glu Val Lys Ser
1               5                   10                  15

Ala Phe Leu Phe Leu Ser Ile Leu Glu Phe Thr Val Gly Val Leu Ala
            20                  25                  30

Asn Ala Phe Ile Phe Leu Val Asn Phe Trp Asp Val Val Arg Lys Gln
        35                  40                  45

Pro Leu Ser Asn Cys Asp Leu Ile Leu Leu Ser Leu Ser Leu Thr Arg
    50                  55                  60

Leu Phe Leu His Gly Leu Leu Phe Leu Asp Ala Leu Gln Leu Thr Tyr
65                  70                  75                  80

Phe Gln Arg Met Lys Asp Pro Leu Ser Leu Ser Tyr Gln Thr Ile Ile
                85                  90                  95

Met Leu Trp Met Ile Thr Asn Gln Val Gly Leu Trp Leu Thr Thr Cys
            100                 105                 110

Leu Ser Leu Leu Tyr Cys Ser Lys Ile Ala Arg Phe Ser His Thr Leu
        115                 120                 125

Leu His Cys Val Ala Ser Trp Val Ser Arg Lys Val Pro Gln Met Leu
    130                 135                 140

Leu Gly Ala Met Leu Phe Ser Cys Ile Cys Thr Ala Ile Cys Leu Gly
145                 150                 155                 160

Asp Phe Phe Ser Arg Ser Gly Phe Thr Phe Thr Thr Met Leu Phe Val
                165                 170                 175

Asn Asn Thr Glu Phe Asn Leu Gln Ile Ala Lys Leu Ser Phe Tyr His
            180                 185                 190

Ser Phe Ile Phe Cys Thr Leu Ala Ser Ile Pro Ser Leu Leu Phe Phe
        195                 200                 205

Leu Ile Ser Ser Gly Val Leu Ile Val Ser Leu Gly Arg His Met Arg
    210                 215                 220

Thr Met Arg Ala Lys Thr Lys Asp Ser His Asp Pro Ser Leu Glu Ala
225                 230                 235                 240

His Ile Lys Ala Leu Arg Ser Leu Val Ser Phe Leu Cys Leu Tyr Val
                245                 250                 255

Val Ser Phe Cys Ala Ala Leu Val Ser Val Pro Leu Leu Met Leu Trp
            260                 265                 270

His Asn Lys Ile Gly Val Met Ile Cys Val Gly Ile Leu Ala Ala Cys
        275                 280                 285

Pro Ser Ile His Ala Ala Ile Leu Ile Ser Gly Asn Ala Lys Leu Arg
    290                 295                 300

Arg Ala Val Glu Thr Ile Leu Leu Trp Val Gln Asn Ser Leu Lys Ile
305                 310                 315                 320

Gly Ala Asp His Lys Ala Asp Ala Arg Thr Pro Gly Leu Cys
                325                 330
```

<210> SEQ ID NO 19
<211> LENGTH: 969
<212> TYPE: DNA
<213> ORGANISM: Felis catus

<400> SEQUENCE: 19

```
atgttagccg gactggataa aatctttctt acgctgtcaa cggcagaatt cgtaattgga      60
atgtcgggga atgtgttcgt tggactggtg aactgctctg aatggatcaa gaaccaaaaa     120
atctcttttg ttgacttcat cctcacctgc ttggctctct cccgaatcac tcagctgctg     180
gtgtcactgt ggcaatcatt cgtaatgaca ctatctccgc ctttctattc cacttggaaa     240
tcagcaaaac ttattacttt gctttggaga ataacgaatc actggactac ctggtttacc     300
acctgcctga gcattttcta cctccttaaa atagctcact tctcccactc tttcttcctc     360
tggctgaagt ggagaacgaa cagagtggtt cttgccattc ttgtcctttc tttgcccttt     420
ctgctgtttg acttcctggt gctagaatca ttgaatgatt tcttcttaaa cgtctatgtg     480
atggatgaaa gtaatctgac attacataca aatgactgta aaagccttta tattaaaacc     540
ctgattcttc ttagtttttc ctataccatt cctattgttc tgtccctgac ctcactggtc     600
ctattgtttc tgtccttggt aagacacatc agaaatttgc agctcaacgt catgggctcc     660
ggggacgcca gcacacaggc ccataagggg gccattaaaa tggttatgtc tttcctcctc     720
ctcttcacgg ttcatttttt ttccatccaa ttgacaaact ggatgctttt gatattttgg     780
aacaacaagt tcacaaagtt tatcatgttg gccatatatg tcttcccctc aggccactcg     840
ttaattttga ttctgggaaa cagcaaactg agacagacag ccttgaaggt actgcggcat     900
cttaaaagca ccttgaaaag agaaaaaaca gtttcgtctt tacagataga cgttccaggg     960
tctttctaa                                                              969
```

<210> SEQ ID NO 20
<211> LENGTH: 322
<212> TYPE: PRT
<213> ORGANISM: Felis catus

<400> SEQUENCE: 20

```
Met Leu Ala Gly Leu Asp Lys Ile Phe Leu Thr Leu Ser Thr Ala Glu
1               5                   10                  15

Phe Val Ile Gly Met Ser Gly Asn Val Phe Val Gly Leu Val Asn Cys
            20                  25                  30

Ser Glu Trp Ile Lys Asn Gln Lys Ile Ser Phe Val Asp Phe Ile Leu
        35                  40                  45

Thr Cys Leu Ala Leu Ser Arg Ile Thr Gln Leu Leu Val Ser Leu Trp
    50                  55                  60

Gln Ser Phe Val Met Thr Leu Ser Pro Pro Phe Tyr Ser Thr Trp Lys
65                  70                  75                  80

Ser Ala Lys Leu Ile Thr Leu Leu Trp Arg Ile Thr Asn His Trp Thr
                85                  90                  95

Thr Trp Phe Thr Thr Cys Leu Ser Ile Phe Tyr Leu Leu Lys Ile Ala
            100                 105                 110

His Phe Ser His Ser Phe Phe Leu Trp Leu Lys Trp Arg Thr Asn Arg
        115                 120                 125

Val Val Leu Ala Ile Leu Val Leu Ser Leu Pro Phe Leu Leu Phe Asp
    130                 135                 140

Phe Leu Val Leu Glu Ser Leu Asn Asp Phe Phe Leu Asn Val Tyr Val
145                 150                 155                 160
```

Met Asp Glu Ser Asn Leu Thr Leu His Thr Asn Asp Cys Lys Ser Leu
            165                 170                 175

Tyr Ile Lys Thr Leu Ile Leu Leu Ser Phe Tyr Thr Ile Pro Ile
        180                 185                 190

Val Leu Ser Leu Thr Ser Leu Val Leu Leu Phe Leu Ser Leu Val Arg
            195                 200                 205

His Ile Arg Asn Leu Gln Leu Asn Val Met Gly Ser Gly Asp Ala Ser
            210                 215                 220

Thr Gln Ala His Lys Gly Ala Ile Lys Met Val Met Ser Phe Leu Leu
225                 230                 235                 240

Leu Phe Thr Val His Phe Phe Ser Ile Gln Leu Thr Asn Trp Met Leu
                245                 250                 255

Leu Ile Phe Trp Asn Asn Lys Phe Thr Lys Phe Ile Met Leu Ala Ile
                260                 265                 270

Tyr Val Phe Pro Ser Gly His Ser Leu Ile Leu Ile Leu Gly Asn Ser
                275                 280                 285

Lys Leu Arg Gln Thr Ala Leu Lys Val Leu Arg His Leu Lys Ser Thr
            290                 295                 300

Leu Lys Arg Glu Lys Thr Val Ser Ser Leu Gln Ile Asp Val Pro Gly
305                 310                 315                 320

Ser Phe

<210> SEQ ID NO 21
<211> LENGTH: 900
<212> TYPE: DNA
<213> ORGANISM: Felis catus

<400> SEQUENCE: 21
atggtaaccg cgctaccgag catttttttcc atcgtggtaa taatagaatt tctcctagga      60
aattttgcca atggcttcat agcactggtg aacttcattg actggaccaa agacaaaag     120 atctcctcag ttgatcacat tctcactgct ctggctgtct ccagaattgg tttgctctgg     180
gtaatattaa taaattggta tgcaactttg ttcagtccag atttctatag cttagaagta     240
agaattattt ttcaaactgc ctggacagta agcaatcatt ttagcatctg gctggctact     300
agcctcagca tattttattt gttcaaaata gccaacttct ccagccttat ttttcttcgc     360
ctcaagtgga gagttaaaag catagttctt gtgattctgt gggggtcctt gttcttttg      420 gtttgtcatg ttgtggcggt gagcgtatgt gagaaagtgc agactgacgt atatgaagga     480
aacggcacta ggaagaccaa attgagggac atttttacagc tttcaaatat gactatattc     540
acactagcaa acttcatacc ctttggtatg tccctgacgt cttttgtgct gttgatcttt     600
tccctctgga aacatctcaa gaggatgcag ctctgtgata agggatctca agatcccagc     660
accaaggtcc acataagagc catgcagacc gtggtctcct ttctcttgtt ctttgccggt     720
tacttcttta ctctgacgat cacaatttgg agttctaatt ggccgcagaa cgagttcggc     780
ttcctccttt gccaggttat tggaatccta tatccttcaa tccactcgtt gatgctgatt     840
cggggaaaca agaagctaag acaggccttt ctgtcatttc tgtggcagct gaagtgctga     900

<210> SEQ ID NO 22
<211> LENGTH: 299
<212> TYPE: PRT
<213> ORGANISM: Felis catus

<400> SEQUENCE: 22

Met Val Thr Ala Leu Pro Ser Ile Phe Ser Ile Val Ile Ile Glu
1               5                   10                  15

Phe Leu Leu Gly Asn Phe Ala Asn Gly Phe Ile Ala Leu Val Asn Phe
            20                  25                  30

Ile Asp Trp Thr Lys Arg Gln Lys Ile Ser Ser Val Asp His Ile Leu
            35                  40                  45

Thr Ala Leu Ala Val Ser Arg Ile Gly Leu Leu Trp Val Ile Leu Ile
        50                  55                  60

Asn Trp Tyr Ala Thr Leu Phe Ser Pro Asp Phe Tyr Ser Leu Glu Val
65                  70                  75                  80

Arg Ile Ile Phe Gln Thr Ala Trp Thr Val Ser Asn His Phe Ser Ile
                85                  90                  95

Trp Leu Ala Thr Ser Leu Ser Ile Phe Tyr Leu Phe Lys Ile Ala Asn
            100                 105                 110

Phe Ser Ser Leu Ile Phe Leu Arg Leu Lys Trp Arg Val Lys Ser Ile
            115                 120                 125

Val Leu Val Ile Leu Leu Gly Ser Leu Phe Phe Leu Val Cys His Val
        130                 135                 140

Val Ala Val Ser Val Cys Glu Lys Val Gln Thr Asp Val Tyr Glu Gly
145                 150                 155                 160

Asn Gly Thr Arg Lys Thr Lys Leu Arg Asp Ile Leu Gln Leu Ser Asn
                165                 170                 175

Met Thr Ile Phe Thr Leu Ala Asn Phe Ile Pro Phe Gly Met Ser Leu
            180                 185                 190

Thr Ser Phe Val Leu Leu Ile Phe Ser Leu Trp Lys His Leu Lys Arg
            195                 200                 205

Met Gln Leu Cys Asp Lys Gly Ser Gln Asp Pro Ser Thr Lys Val His
        210                 215                 220

Ile Arg Ala Met Gln Thr Val Val Ser Phe Leu Leu Phe Phe Ala Gly
225                 230                 235                 240

Tyr Phe Phe Thr Leu Thr Ile Thr Ile Trp Ser Ser Asn Trp Pro Gln
                245                 250                 255

Asn Glu Phe Gly Phe Leu Leu Cys Gln Val Ile Gly Ile Leu Tyr Pro
            260                 265                 270

Ser Ile His Ser Leu Met Leu Ile Arg Gly Asn Lys Lys Leu Arg Gln
            275                 280                 285

Ala Phe Leu Ser Phe Leu Trp Gln Leu Lys Cys
        290                 295

<210> SEQ ID NO 23
<211> LENGTH: 927
<212> TYPE: DNA
<213> ORGANISM: Felis catus

<400> SEQUENCE: 23
atggtaagcg cgctaccaag cattttttcc attgcggtaa taatagaatt tctcctagga    60
aattttgcca atggcttcat agcactggtg aacttcattg actggaccaa gagacaaaag   120
atctcctcag ttgatcacat tctcgctgct ctggctgtct ccagaattgg tttgctctgg   180
gtaatgataa taaattggta tgcaacttgg ttcagtccag atttcaagag cttagaagta   240
agaattattt ttcaaactgc ctggacagta agcaatcatt ttagcatctg gctggctact   300
agcctcagca tatttatttt gttcaaaata gccaacttct ccagcctat tttccttcgc   360 ctcaagtgga gagttaaaag cgtcgtgctt gtgatgctgc tggggtcttt gttcttattg   420

```
tttctcatg tggcggcagt gagcatatat gagaaagtgc agactaaggc atatgaaggg    480
aatgtcactt ggaggaccaa atggacgggc atggcacacc tctcaaatat gactgtattc    540
acactagcaa acttcatacc cttttgctacg tccctgacgt cttttgtgct gttgatcttt    600
tccctctgga gacatctcaa gcggatgcag ctctgtggca agggatccca agatcccagc    660
accaaggtcc acataagagc catgcagacg gtggtctcct ttctcttgtt ctttgccggt    720
tacgttctga atctaattgt tacagtttgg agttttaacg ggctgcagaa ggaactgttc    780
atgttttgcc aggtacttgc cttcgtgtat ccttcgatcc actcgctgat gttgatttgg    840
ggaaacaaga agctaaaaca ggcctttctg tctgttttat accaggagaa gtactggctg    900
aaagaacaga aacactcaac tccatag                                        927
```

```
<210> SEQ ID NO 24
<211> LENGTH: 308
<212> TYPE: PRT
<213> ORGANISM: Felis catus

<400> SEQUENCE: 24

Met Val Ser Ala Leu Pro Ser Ile Phe Ser Ile Ala Val Ile Ile Glu
1               5                   10                  15

Phe Leu Leu Gly Asn Phe Ala Asn Gly Phe Ile Ala Leu Val Asn Phe
            20                  25                  30

Ile Asp Trp Thr Lys Arg Gln Lys Ile Ser Ser Val Asp His Ile Leu
        35                  40                  45

Ala Ala Leu Ala Val Ser Arg Ile Gly Leu Leu Trp Val Met Ile Ile
    50                  55                  60

Asn Trp Tyr Ala Thr Trp Phe Ser Pro Asp Phe Lys Ser Leu Glu Val
65                  70                  75                  80

Arg Ile Ile Phe Gln Thr Ala Trp Thr Val Ser Asn His Phe Ser Ile
                85                  90                  95

Trp Leu Ala Thr Ser Leu Ser Ile Phe Tyr Leu Phe Lys Ile Ala Asn
            100                 105                 110

Phe Ser Ser Leu Ile Phe Leu Arg Leu Lys Trp Arg Val Lys Ser Val
        115                 120                 125

Val Leu Val Met Leu Leu Gly Ser Leu Phe Leu Phe Ser His Val
    130                 135                 140

Ala Ala Val Ser Ile Tyr Glu Lys Val Gln Thr Lys Ala Tyr Glu Gly
145                 150                 155                 160

Asn Val Thr Trp Arg Thr Lys Trp Thr Gly Met Ala His Leu Ser Asn
                165                 170                 175

Met Thr Val Phe Thr Leu Ala Asn Phe Ile Pro Phe Ala Thr Ser Leu
            180                 185                 190

Thr Ser Phe Val Leu Leu Ile Phe Ser Leu Trp Arg His Leu Lys Arg
        195                 200                 205

Met Gln Leu Cys Gly Lys Gly Ser Gln Asp Pro Ser Thr Lys Val His
    210                 215                 220

Ile Arg Ala Met Gln Thr Val Val Ser Phe Leu Leu Phe Phe Ala Gly
225                 230                 235                 240

Tyr Val Leu Asn Leu Ile Val Thr Val Trp Ser Phe Asn Gly Leu Gln
                245                 250                 255

Lys Glu Leu Phe Met Phe Cys Gln Val Leu Ala Phe Val Tyr Pro Ser
            260                 265                 270

Ile His Ser Leu Met Leu Ile Trp Gly Asn Lys Lys Leu Lys Gln Ala
        275                 280                 285
```

```
Phe Leu Ser Val Leu Tyr Gln Glu Lys Tyr Trp Leu Lys Glu Gln Lys
    290                 295                 300

His Ser Thr Pro
305

<210> SEQ ID NO 25
<211> LENGTH: 939
<212> TYPE: DNA
<213> ORGANISM: Felis catus

<400> SEQUENCE: 25
atgccatctg gaatcgaaaa tactttctg acagccgcgg taggaacatt catgattgga        60
atgttgggga atggtttcat cgcactcgtc aactgcattg actgggtgaa gcatcgaaag      120
ctctcgccag ctgactgcat cctcaccagc ctggctgtct ccagaatcat tcttctttgg      180
atgatactat tcgatttgct tgtaatggtg ttttggccac atctatataa cattgagaaa      240
ctagctaccg ctgttaatat ctgttggaca ctgaccaatc acctagctac ctggtttgcc      300
acctgcctga gtgttttcta tttctttagg atagccaatt tctcccaccg ctatttcacc      360
tggctgaggc ggagaattag cagggtgctc cctgtgcttc ctctggggtc tttattctta      420
ctggttttca actacaaatt attagttgga ttttctgatc tctgggctac catctaccac      480
aactatgaaa gaaactcaac tcggccccta gatgtaagta aaactgggta tcttaacagc      540
ttggttattc tcagtttcat ctacttaatc cccttccttc tgtccctgac ctcactgctc      600
ctttattttc tctccttgat gagacatacc aggaacgtgc aactgaactc tagctcgagg      660
gacttcagca cggaggccca taaaagggcc atgaaaatgg tgatatcttt cctcctcctc      720
tccacggttc attttttttc catccagtta acaggttgga ttttccttt actgaagaaa      780 catcatgcca acttgacggt gacgttgaca tcggctcttt tccttcagg ccactcattt      840 atcctcattt ttggaaacag caagctgaga caaactgctt taggactact gtggcatctc      900
aattgccacc tgaaaatggt gaaacccttt a gcttcatag                           939

<210> SEQ ID NO 26
<211> LENGTH: 312
<212> TYPE: PRT
<213> ORGANISM: Felis catus

<400> SEQUENCE: 26

Met Pro Ser Gly Ile Glu Asn Thr Phe Leu Thr Ala Ala Val Gly Thr
1               5                   10                  15

Phe Met Ile Gly Met Leu Gly Asn Gly Phe Ile Ala Leu Val Asn Cys
            20                  25                  30

Ile Asp Trp Val Lys His Arg Lys Leu Ser Pro Ala Asp Cys Ile Leu
        35                  40                  45

Thr Ser Leu Ala Val Ser Arg Ile Ile Leu Leu Trp Met Ile Leu Phe
    50                  55                  60

Asp Leu Leu Val Met Val Phe Trp Pro His Leu Tyr Asn Ile Glu Lys
65                  70                  75                  80

Leu Ala Thr Ala Val Asn Ile Cys Trp Thr Leu Thr Asn His Leu Ala
                85                  90                  95

Thr Trp Phe Ala Thr Cys Leu Ser Val Phe Tyr Phe Phe Arg Ile Ala
            100                 105                 110

Asn Phe Ser His Arg Tyr Phe Thr Trp Leu Arg Arg Arg Ile Ser Arg
        115                 120                 125
```

```
Val Leu Pro Val Leu Pro Leu Gly Ser Leu Phe Leu Leu Val Phe Asn
130                 135                 140

Tyr Lys Leu Leu Val Gly Phe Ser Asp Leu Trp Ala Thr Ile Tyr His
145                 150                 155                 160

Asn Tyr Glu Arg Asn Ser Thr Arg Pro Leu Asp Val Ser Lys Thr Gly
                165                 170                 175

Tyr Leu Asn Ser Leu Val Ile Leu Ser Phe Ile Tyr Leu Ile Pro Phe
            180                 185                 190

Leu Leu Ser Leu Thr Ser Leu Leu Leu Phe Leu Ser Leu Met Arg
        195                 200                 205

His Thr Arg Asn Val Gln Leu Asn Ser Ser Ser Arg Asp Phe Ser Thr
210                 215                 220

Glu Ala His Lys Arg Ala Met Lys Met Val Ile Ser Phe Leu Leu Leu
225                 230                 235                 240

Ser Thr Val His Phe Phe Ser Ile Gln Leu Thr Gly Trp Ile Phe Leu
                245                 250                 255

Leu Leu Lys Lys His His Ala Asn Leu Thr Val Thr Leu Thr Ser Ala
            260                 265                 270

Leu Phe Pro Ser Gly His Ser Phe Ile Leu Ile Phe Gly Asn Ser Lys
        275                 280                 285

Leu Arg Gln Thr Ala Leu Gly Leu Leu Trp His Leu Asn Cys His Leu
290                 295                 300

Lys Met Val Lys Pro Leu Ala Ser
305                 310

<210> SEQ ID NO 27
<211> LENGTH: 299
<212> TYPE: PRT
<213> ORGANISM: Homo sapiens

<400> SEQUENCE: 27

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Leu Lys Arg Asn Ile Ser Pro Lys
        115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190
```

Val Thr Ser Ala Ser Leu Leu Ile His Ser Leu Arg Arg His Ile Gln
            195                 200                 205

Lys Met Gln Lys Asn Ala Thr Gly Phe Trp Asn Pro Gln Thr Glu Ala
    210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
                260                 265                 270

Ser Pro Gly His Ser Val Leu Ile Ile Ile Thr His Pro Lys Leu Lys
                275                 280                 285

Thr Thr Ala Lys Lys Ile Leu Cys Phe Lys Lys
            290                 295

<210> SEQ ID NO 28
<211> LENGTH: 312
<212> TYPE: PRT
<213> ORGANISM: Homo sapiens

<400> SEQUENCE: 28

Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
                20                  25                  30

Ile Asp Trp Leu Lys Arg Arg Asp Ile Ser Leu Ile Asp Ile Ile Leu
            35                  40                  45

Ile Ser Leu Ala Ile Ser Arg Ile Cys Leu Leu Cys Val Ile Ser Leu
50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala
            100                 105                 110

Asn Ile Ser His Pro Phe Phe Phe Trp Leu Lys Leu Lys Ile Asn Lys
            115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
            195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val

```
              260                 265                 270
Ile Phe Pro Ser Ser His Ser Phe Ile Leu Ile Met Gly Asn Ser Lys
            275                 280                 285

Leu Arg Glu Ala Phe Leu Lys Met Leu Arg Phe Val Lys Cys Phe Leu
        290                 295                 300

Arg Arg Arg Lys Pro Phe Val Pro
305                 310

<210> SEQ ID NO 29
<211> LENGTH: 307
<212> TYPE: PRT
<213> ORGANISM: Homo sapiens

<400> SEQUENCE: 29

Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
        35                  40                  45

Gly Leu Ala Ile Ser Arg Ile Phe Leu Ile Trp Ile Ile Thr Asp
50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
290                 295                 300

Arg Val Thr
305
```

<210> SEQ ID NO 30
<211> LENGTH: 291
<212> TYPE: PRT
<213> ORGANISM: Homo sapiens

<400> SEQUENCE: 30

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290

<210> SEQ ID NO 31
<211> LENGTH: 333
<212> TYPE: PRT
<213> ORGANISM: Homo sapiens

<400> SEQUENCE: 31

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

| | | | | | | | | | | | |
|---|---|---|---|---|---|---|---|---|---|---|---|
|Asn|Ala|Phe|Val|Phe|Leu|Val|Asn|Phe|Trp|Asp|Val|Val|Lys|Arg|Gln|
| | |35| | | |40| | | |45| | | | | |
|Ala|Leu|Ser|Asn|Ser|Asp|Cys|Val|Leu|Cys|Leu|Ser|Ile|Ser|Arg|
| |50| | | | |55| | | |60| | | | |
|Leu|Phe|Leu|His|Gly|Leu|Leu|Phe|Leu|Ser|Ala|Ile|Gln|Leu|Thr|His|
|65| | | | |70| | | |75| | | | | |80|
|Phe|Gln|Lys|Leu|Ser|Glu|Pro|Leu|Asn|His|Ser|Tyr|Gln|Ala|Ile|Ile|
| | | | |85| | | |90| | | | |95| |
|Met|Leu|Trp|Met|Ile|Ala|Asn|Gln|Ala|Asn|Leu|Trp|Leu|Ala|Ala|Cys|
| | | |100| | | |105| | | |110| | | |
|Leu|Ser|Leu|Leu|Tyr|Cys|Ser|Lys|Leu|Ile|Arg|Phe|Ser|His|Thr|Phe|
| | |115| | | |120| | | |125| | | | |
|Leu|Ile|Cys|Leu|Ala|Ser|Trp|Val|Ser|Arg|Lys|Ile|Ser|Gln|Met|Leu|
| |130| | | |135| | | |140| | | | | |
|Leu|Gly|Ile|Ile|Leu|Cys|Ser|Cys|Ile|Cys|Thr|Val|Leu|Cys|Val|Trp|
|145| | | |150| | | |155| | | |160| | | |
|Cys|Phe|Phe|Ser|Arg|Pro|His|Phe|Thr|Val|Thr|Thr|Val|Leu|Phe|Met|
| | | |165| | | |170| | | |175| | | | |
|Asn|Asn|Asn|Thr|Arg|Leu|Asn|Trp|Gln|Ile|Lys|Asp|Leu|Asn|Leu|Phe|
| | |180| | | |185| | | |190| | | | | |
|Tyr|Ser|Phe|Leu|Phe|Cys|Tyr|Leu|Trp|Ser|Val|Pro|Pro|Phe|Leu|Leu|
| |195| | | |200| | | |205| | | | | | |
|Phe|Leu|Val|Ser|Ser|Gly|Met|Leu|Thr|Val|Ser|Leu|Gly|Arg|His|Met|
| |210| | | |215| | | |220| | | | | | |
|Arg|Thr|Met|Lys|Val|Tyr|Thr|Arg|Asn|Ser|Arg|Asp|Pro|Ser|Leu|Glu|
|225| | | |230| | | |235| | | |240|
|Ala|His|Ile|Lys|Ala|Leu|Lys|Ser|Leu|Val|Ser|Phe|Phe|Cys|Phe|Phe|
| | | |245| | | |250| | | |255| | | | |
|Val|Ile|Ser|Ser|Cys|Val|Ala|Phe|Ile|Ser|Val|Pro|Leu|Leu|Ile|Leu|
| | |260| | | |265| | | |270| | | | | |
|Trp|Arg|Asp|Lys|Ile|Gly|Val|Met|Val|Cys|Val|Gly|Ile|Met|Ala|Ala|
| |275| | | |280| | | |285| | | | | | |
|Cys|Pro|Ser|Gly|His|Ala|Ala|Ile|Leu|Ile|Ser|Gly|Asn|Ala|Lys|Leu|
| |290| | | |295| | | |300| | | | | | |
|Arg|Arg|Ala|Val|Met|Thr|Ile|Leu|Leu|Trp|Ala|Gln|Ser|Ser|Leu|Lys|
|305| | | |310| | | |315| | | |320|
|Val|Arg|Ala|Asp|His|Lys|Ala|Asp|Ser|Arg|Thr|Leu|Cys|
| | | |325| | | |330| | | | | |